US011450003B2

(12) United States Patent
Li et al.

(10) Patent No.: US 11,450,003 B2
(45) Date of Patent: Sep. 20, 2022

(54) MEDICAL IMAGING APPARATUS, IMAGE PROCESSING APPARATUS, AND IMAGE PROCESSING METHOD

(71) Applicant: Hitachi, Ltd., Tokyo (JP)

(72) Inventors: Yun Li, Tokyo (JP); Takashi Toyomura, Tokyo (JP); Kenta Inoue, Tokyo (JP); Toshinori Maeda, Tokyo (JP)

(73) Assignee: FUJIFILM HEALTHCARE CORPORATION, Chiba (JP)

( * ) Notice: Subject to any disclaimer, the term of this patent is extended or adjusted under 35 U.S.C. 154(b) by 72 days.

(21) Appl. No.: 16/594,116

(22) Filed: Oct. 7, 2019

(65) Prior Publication Data

US 2020/0134825 A1  Apr. 30, 2020

(30) Foreign Application Priority Data

Oct. 29, 2018  (JP) .............................. JP2018-202441

(51) Int. Cl.
  *G06T 7/11* (2017.01)
  *G06T 7/00* (2017.01)
  (Continued)

(52) U.S. Cl.
  CPC .............. *G06T 7/11* (2017.01); *A61B 6/5205* (2013.01); *A61B 8/483* (2013.01); *A61B 8/5207* (2013.01);
  (Continued)

(58) Field of Classification Search
  CPC ...... G06N 3/08; G06N 3/0454; G06T 7/0012; G06T 7/11; G06T 11/003; G06T 2200/04;
  (Continued)

(56) References Cited

U.S. PATENT DOCUMENTS

2008/0253631 A1* 10/2008 Oosawa ................. G16H 15/00
                                                    382/128
2011/0311116 A1* 12/2011 Benn ...................... G06T 11/00
                                                    382/128

(Continued)

FOREIGN PATENT DOCUMENTS

JP    2016-168046 A    9/2016
JP    2018-22484 A     2/2018

(Continued)

OTHER PUBLICATIONS

Japanese Office Action received in corresponding Japanese Application No. 2018-202441 dated May 17, 2022.

*Primary Examiner* — Katrina R Fujita
(74) *Attorney, Agent, or Firm* — Mattingly & Malur, PC

(57) ABSTRACT

Provided is a technology for extracting an image of a target plane from 2D or 3D image data acquired by a medical imaging apparatus with a small amount of computation and at high speed. A plane of a target plane including a predetermined structure is extracted from image data of a subject. A region of the predetermined structure included in the plane is detected by applying a learning model learned using learning data including a target plane for learning including an image of the structure and a region-of-interest plane for learning obtained by cutting out and enlarging a partial region including the structure in the target plane for learning to a plurality of planes obtained from the image data, and the plane of the target plane is extracted based on the detected region of the predetermined structure.

11 Claims, 21 Drawing Sheets

(51) Int. Cl.
*A61B 8/08* (2006.01)
*A61B 6/00* (2006.01)
*G06N 3/08* (2006.01)
*G06T 11/00* (2006.01)

(52) U.S. Cl.
CPC ............ *G06N 3/08* (2013.01); *G06T 7/0012* (2013.01); *G06T 11/003* (2013.01); *G06T 2200/04* (2013.01); *G06T 2207/10* (2013.01); *G06T 2207/30004* (2013.01)

(58) Field of Classification Search
CPC ............ G06T 2200/24; G06T 2207/10; G06T 2207/10076; G06T 2207/30004; A61B 6/032; A61B 6/5205; A61B 8/483; A61B 8/488; A61B 8/5207
See application file for complete search history.

(56) References Cited

U.S. PATENT DOCUMENTS

2018/0000444 A1* 1/2018 Dayton ................ A61B 8/0883
2018/0039853 A1* 2/2018 Liu ......................... G06K 9/72

FOREIGN PATENT DOCUMENTS

| JP | 2018-79000 A | 5/2018 |
| JP | 2018-151748 A | 9/2018 |
| WO | 2012/042808 A1 | 4/2012 |
| WO | 2016/190256 A1 | 12/2016 |

\* cited by examiner

FIG. 7
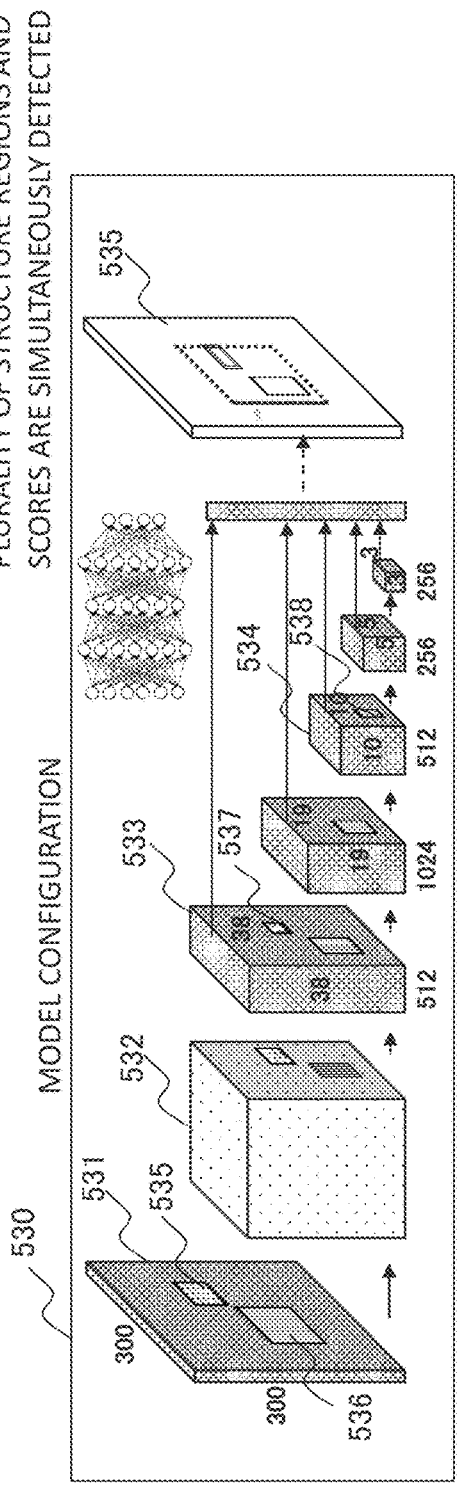
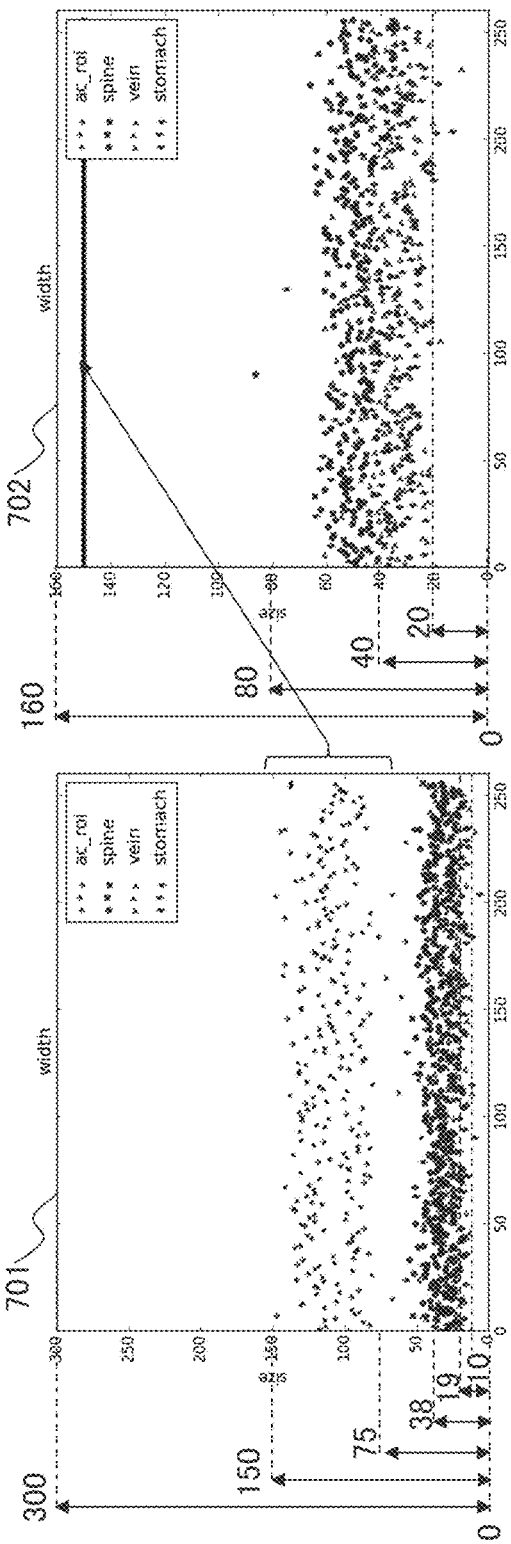

SHAPE SCORE: $Score_{shape} = \sum_{i=0}^{n} W_i S_i;$ ··· (1)
($S_i$: DETECTION SCORE OF STRUCTURE i (NONE → 0), $W_i$: WEIGHT OF STRUCTURE i)

GEOMETRIC SCORE: $Score_{geometry} = \sum_{j=0}^{m} W'_j G_j;$ ··· (2)
($G_j$: COMPUTATION SCORE OF GEOMETRIC REFERENCE j,
$W'_j$: WEIGHT OF GEOMETRIC REFERENCE j)

TOTAL SCORE: $Score_{total} = Score_{shape} + Score_{geometry}$ ··· (3)

MEDICAL IMAGING APPARATUS, IMAGE PROCESSING APPARATUS, AND IMAGE PROCESSING METHOD

CROSS-REFERENCE TO RELATED APPLICATION

The present application claims priority from Japanese application JP2018-202441, filed on Oct. 29, 2018, the contents of which is hereby incorporated by reference into this application.

BACKGROUND OF THE INVENTION

Field of the Invention

The present invention relates to a medical imaging apparatus such as an ultrasonic diagnostic apparatus, an MRI apparatus, or a CT apparatus, and particularly relates to a technology for selecting a predetermined plane from a three-dimensional (3D) image or a time series two-dimensional (2D) or time series 3D image acquired by the medical imaging apparatus, and displaying the selected plane.

Description of the Related Art

The medical imaging apparatus is used not only for displaying an image after acquiring a form image of a target part, but also for a purpose of quantitatively acquiring form information or function information. Examples of such a purpose include estimated weight measurement for observing fetal growth in an ultrasonic diagnostic apparatus. Such measurement is roughly divided into three processes of image acquisition, measurement image selection, and measurement. First, in the image acquisition process, a plurality of 2D planes continuously captured from around the target region or volume data is acquired. Subsequently, in the measurement image selection process, an optimum plane for measurement is selected from the acquired data. Then, in the measurement process, in the case of estimated weight measurement for a fetus, each part of a head, an abdomen, and a leg is measured, and calculation according to a predetermined calculation formula is performed on a measurement value to compute the weight. Measurement of the head and abdomen requires a surface trace, and thus it took a long time for inspection. In recent years, however, an automatic measurement technology has been proposed in which the trace is automatically performed up to a predetermined calculation (International Patent Application No. 2016/190256, etc.). This technology has improved a work flow for the measurement process.

However, in inspection, the most time-consuming and labor-intensive process is the measurement image selection process after the image acquisition. Especially when the target is a fetus, it is necessary to select an optimal plane for measurement from a plane obtained by estimating a location of a target plane for the fetus present inside an abdomen of a subject, and there is a problem that it takes time. To cope with such a problem, International Patent Application No. 2012/042808 discloses a technology for extracting a high-echo region from 3D data and selecting a target plane based on a 3D feature of the extracted high-echo region. Specifically, a template showing a 3D feature prepared in advance and a 3D feature of the extracted high-echo region are matched, and a direction of the target plane is determined from template data to determine a plurality of target planes (sections) when the template coincides with the 3D feature.

In general, as a feature of an ultrasonic image, image data to be captured varies each time an imaging person (inspector) varies or each time an imaging sequence (imaging time) varies (imaging person dependency). In addition, image data to be captured varies depending on the constitution or disease of the imaging target (imaging target dependency). The imaging person dependency occurs since an ultrasonic wave is irradiated and a region in a body acquired as a plane or volume data is manually searched for each time imaging is performed, and thus it is difficult to completely match acquired data even when the same inspector performs inspection on the same patient. In addition, the imaging target dependency occurs since an internal propagation speed and attenuation rate of ultrasound differ depending on the constitution of the patient, the shape of an organ does not completely match between patients depending on the disease of the patient and individual differences. Furthermore, when specializing in obstetrics, there are uncertain factors that affect imaging. For example, a fetus in an abdomen of a pregnant woman greatly increases in size according to a development process, and a position and a posture at the time of imaging vary each time imaging is performed. That is, an ideal plane for measurement is difficult to obtain because it is affected by the imaging person dependency and the imaging target dependency. In addition, the acquired data includes a deviation from an ideal position, an uncertain size, a blurred image, a characteristic shape difference, etc.

The technology disclosed in International Patent Application No. 2012/042808 has difficulty in coping with the imaging person dependency or the imaging target dependency since a plane is determined by matching with a template prepared in advance.

On the other hand, an image acquired by an MRI apparatus or a CT apparatus is less dependent on the imaging person dependency when compared to an ultrasonic image and has the imaging target dependency. When there is a change in form in a time-series image of a heart or lung, it is not easy to determine a plane by matching with a template.

In addition, in recent years, attempts have been made to apply a deep learning (DL) technology to improve image quality, determine a specific disease, etc. However, to achieve high-accuracy discrimination using DL, hardware having high processing capability is necessary, and a long time is required for processing. Thus, mounting on a conventional medical imaging apparatus or a medical imaging apparatus that requires high-speed processing is difficult.

SUMMARY OF THE INVENTION

Therefore, an object of the invention is to provide a technology for extracting an image of a target plane from 2D or 3D image data acquired by a medical imaging apparatus with a small amount of computation and at high speed.

As one aspect, the invention provides a medical imaging apparatus including an imaging unit that collects image data of a subject, and an image processing unit that performs a process of extracting a plane of a target plane from the image data collected by the imaging unit. The image processing unit includes a learning model storage unit that stores a learning model learned using learning data, a structure extraction unit that detects a region of the predetermined structure included in the plane by applying the learning model to a plurality of planes obtained from the image data, and a plane extraction unit that extracts the plane of the target plane from the plurality of planes based on the detected region of the predetermined structure. The learning data includes a target plane for learning including an image of the structure captured in advance for the target plane, and a region-of-interest plane for learning obtained by cutting out and enlarging a partial region including the structure in the target plane for learning. For example, a reduced model, in which at least one of an input image size and the number of levels of a high-accuracy model learned using the target plane as learning data is reduced based on analysis of a relative size of a detection target region, is used as the learning model.

The present application claims priority from Japanese patent application JP-2018-202441 filed on Oct. 29, 2018, the content of which is hereby incorporated by reference into this application.

According to the invention, since a learning model has learned learning data of a plurality of scales of a target plane and a region-of-interest plane and a predetermined internal structure, it is possible to extract an image of a target plane from 2D or 3D image data acquired by a medical imaging apparatus with a small amount of computation and at high speed by extracting structures step by step by this learning model and using the extracted structures for plane evaluation by the structures.

BRIEF DESCRIPTION OF THE DRAWINGS

FIG. 7 is a diagram illustrating a configuration of a basic model and a size distribution of a structure;

DETAILED DESCRIPTION OF THE INVENTION

Hereinafter, embodiments of the invention will be described with reference to drawings.

First Embodiment

Figure 1:
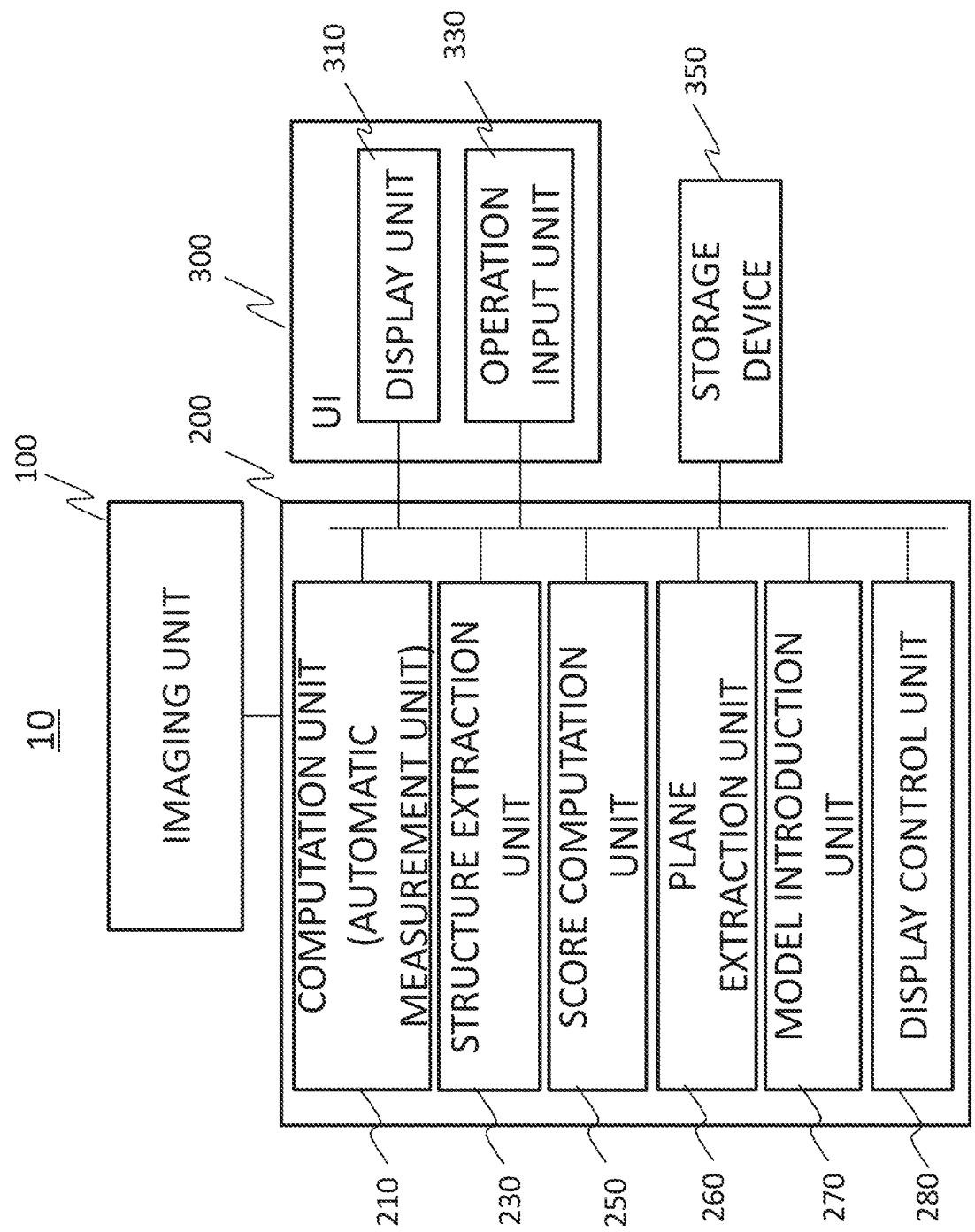
FIG. 1 is a diagram illustrating an overall configuration of a medical imaging apparatus of a first embodiment.

As illustrated in FIG. 1, a medical imaging apparatus 10 of the present embodiment at least includes an imaging unit 100 that captures an image of a subject and collects image data, and an image processing unit 200 that performs a process of extracting a plane of a target plane including a predetermined structure from the image data collected by the imaging unit 100. In an example of FIG. 1, the medical imaging apparatus 10 further includes a display unit 310 that displays an image acquired by the imaging unit 100 or an image processed by the image processing unit 200, and an operation input unit 330 for inputting a command or data necessary for processing of the imaging unit 100 or the image processing unit 200 by a user. The display unit 310 and the operation input unit 330 are usually arranged close to each other and function as a user interface (UI) 300. The medical imaging apparatus 10 may further include a storage device 350 that stores image data obtained by the imaging unit 100, data used for processing by the image processing unit 200, a processing result, etc.

A configuration of the imaging unit 100 varies depending on the modality. In the case of an MRI apparatus, a magnetic field generation unit for collecting a magnetic resonance signal from a subject placed in a static magnetic field is provided. In the case of a CT apparatus, an X-ray source that irradiates the subject with an X-ray, an X-ray detector that detects an X-ray transmitted through the subject, and a mechanism for rotating the X-ray source and the X-ray detector around the subject are provided. The ultrasonic diagnostic apparatus includes a unit for transmitting an ultrasonic wave to a subject and receiving an ultrasonic wave that is a reflected wave from the subject to generate an ultrasonic image. A scheme of generating image data in the imaging unit differs depending on the modality. Finally, volume data (3D image data), time-series 2D image data, or time-series volume data is obtained. Hereinafter, these data will be collectively described as image data.

Figure 2:
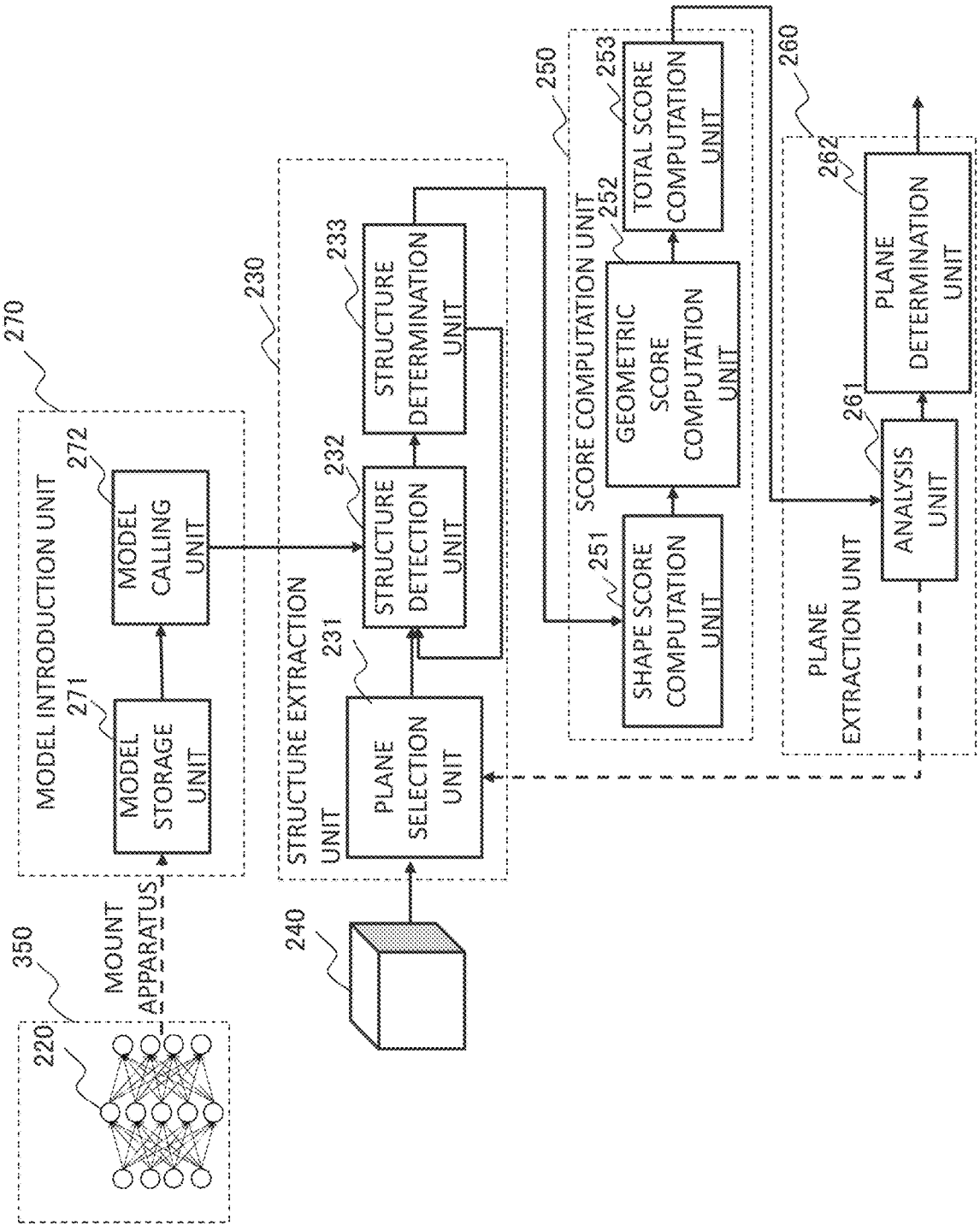
FIG. 2 is a diagram illustrating a configuration of a main part of an image processing unit of the first embodiment.

As illustrated in FIG. 1 and FIG. 2, the image processing unit 200 includes a model introduction unit 270 including a learning model storage unit 271 that stores a learning model learned using learning data, a structure extraction unit 230 that detects a region of a predetermined structure included in a plane by applying the learning model to a plurality of planes obtained from image data, and a plane extraction unit 260 that extracts a plane of a target plane from a plurality of planes based on the detected region of the predetermined structure.

In addition, the target plane varies depending on the purpose of diagnosis or the purpose of image processing for the plane. Here, the target plane is a plane suitable for measuring a size (width, length, diameter, circumference length, etc.) or a position (relative angle, relative length) of a structure (for example, a predetermined organ or part) included in the plane.

A learning model used by the structure extraction unit 230 is a learned machine learning model using learning data. For example, the learning model can be configured by a convolutional neural network (CNN). The learning data includes a target plane for learning including an image of a predetermined structure captured in advance with respect to the target plane, and a region-of-interest plane for learning obtained by cutting out and enlarging a partial region including a predetermined structure from the target plane for learning.

As described above, the learning model of the present embodiment is learned by two or more types of target plane for learnings having different enlargement rates, that is, the target plane for learning and the region-of-interest plane for learning obtained by enlarging a part thereof. Therefore, it is possible to narrow down an attention region step by step like a pyramid in an extraction stage to perform multi-stage extraction, and it is possible to shorten a processing time of the image processing unit 200 while maintaining high extraction accuracy.

In the following description, learning data including target tomographic images for learning having different enlargement rates is also referred to as multi-scale learning data or learning data of a plurality of scales.

It is desirable that the learning data includes information for specifying a type of the structure (for example, a name of the structure (spine, umbilical vein, stomach, etc.) and position information of a region where the structure is located on the image (for example, coordinates of the region) corresponding to each of the target plane for learning or the region-of-interest plane for learning including the structure.

As a multi-stage extraction method, for example, the structure extraction unit 230 first applies a learning model learned by multi-scale learning data to a plane obtained from image data, thereby obtaining a structure included in the plane. Subsequently, the structure extraction unit 230 generates an image obtained by cutting out a region including the detected structure from the plane, and applies the learning model again. In this way, the structure contained in the cut-out image is further detected. In this way, the structure can be detected in multiple stages.

Specifically, for example, when a first structure and a second structure located inside the first structure are included in the target plane as the structure, the target plane for learning of the learning data includes images of the first structure and the second structure. In this case, as the region-of-interest plane for learning, an image obtained by cutting out and enlarging a partial region including the first structure of the target plane can be used. When the first structure is detected by applying the learning model to the plane obtained from the image data, the structure extraction unit 230 can generate an image obtained by cutting out the region including the first structure from the plane, apply the learning model to the cut image, and detect the second structure.

By performing multi-stage extraction, the amount of computation at each stage can be reduced, and thus it is possible to detect multiple structures of different scales with high accuracy at high speed using a reduced learning model (also referred to as a reduced model).

As the reduced model, a reduced model in which at least one of an input image size and the number of levels of a learned high-accuracy model is reduced using the target plane as learning data is used. The input image size, the number of levels, and a corresponding region size in each layer are designed based on distribution analysis of relative sizes of a structure to be detected, a target plane, and a region-of-interest plane. The reduced model is relearned by learning data including the target plane for learning and the region-of-interest plane for learning. When the learning model is a model in which the input image size is reduced, the structure extraction unit 230 may reduce the plane obtained from the image data to the input image size and input the image to the learning model as an input image. In other words, as the learning model, an optimized reduced model is used based on distribution analysis of relative sizes of a predetermined structure, a target plane, and a region-of-interest plane.

The reduced model has a small amount of computation, and thus can be mounted on a computation unit of the medical imaging apparatus. A specific structure and learning process of the learning model will be described in detail in a second embodiment described later.

The learning model (reduced model) is created in advance by the medical imaging apparatus 10 or by a calculator, etc. independent of the medical imaging apparatus 10 and stored in the storage device 350, for example. When there is a plurality of target planes (identification tasks) to be identified, a plurality of types of reduced models may be created, or a model created by learning structures having different planes in one model may be used. For example, when there is a plurality of measurement targets (head, chest, leg, etc.) and the target plane is present for each measurement target, the learning model is created for each target plane of the measurement target (head, chest, and leg). In addition, when there is a plurality of types of target planes (for example, different plane orientations) for one measurement part, creation is performed according to the type of target plane. Any one or more created learning models are stored in the storage device 350.

The image processing unit 200 includes a score computation unit 250, a computation unit 210, and a display control unit 280, in addition to the model introduction unit 270, the structure extraction unit 230, and the plane extraction unit 260.

As illustrated in FIG. 2, the model introduction unit 270 includes a model storage unit 271 that reads and stores a learning model 220 suitable for an identification task (target plane to be identified) from a storage device 350, and a model calling unit 273 that calls a learning model from the model storage unit 271 and applies the learning model to the structure extraction unit 230.

In addition, the structure extraction unit 230 includes a plane selection unit 231, a structure detection unit 232, and a structure determination unit 233. The plane selection unit 231 selects a plurality of planes from image data 240 such as volume data or time-series 2D continuous data. The structure detection unit 232 detects (identifies) the presence or absence of a region of a target structure in the plane by applying the learning model read by the model introduction unit 270 to the plane selected by the plane selection unit 231, and outputs a score indicating reliability of the detection (identification) when the region of the structure is detected. The structure determination unit 233 selects a region of the structure having a high reliability score.

The score computation unit 250 includes a shape score computation unit 251 that computes a shape score using a predetermined mathematical formula based on the presence or absence of detection of the structure by the structure extraction unit 230 and a score indicating reliability of each structure, a geometric score computation unit 252 that computes a geometric score from a geometric positional relationship between regions of the structure detected by the structure extraction unit 230, and a total score computation unit 253 that computes a total score from the shape score and the geometric score.

The plane extraction unit 260 includes an analysis unit 261 and a plane determination unit 262. The analysis unit 261 analyzes structure extraction results of a plurality of planes and progresses of values of the shape score, the geometric score, and the total score to perform determination as to whether to end target plane search or determination of a plane group from which a structure is subsequently extracted. Based on an analysis result, the plane determination unit 262 determines, for example, a plane having a highest total score as a plane of the target plane. The analysis unit 261 feeds back the plane group from which the structure is subsequently extracted to the plane selection unit 231 to cause the plane selection unit 231 to perform selection.

The computation unit 210 of the image processing unit 200 performs computation (automatic measurement) of a predetermined measurement value for the image data of the plane extracted by the plane extraction unit 260 using the extracted region of the structure. In addition, other computations may be performed. The display control unit 280 performs control for causing the display unit 310 to display the plane of the target plane selected by the plane extraction unit, the region of the structure, the shape score/the geometric score/the total score, etc. in a predetermined display mode.

Some or all of the functions of the image processing unit 200 can be realized as software executed by the CPU. Further, a part related to image data creation of the imaging unit and a part of the image processing unit may be realized by hardware such as an application specific integrated circuit (ASIC), a field programmable gate array (FPGA), or a graphics processing unit (GPU).

Figure 3:
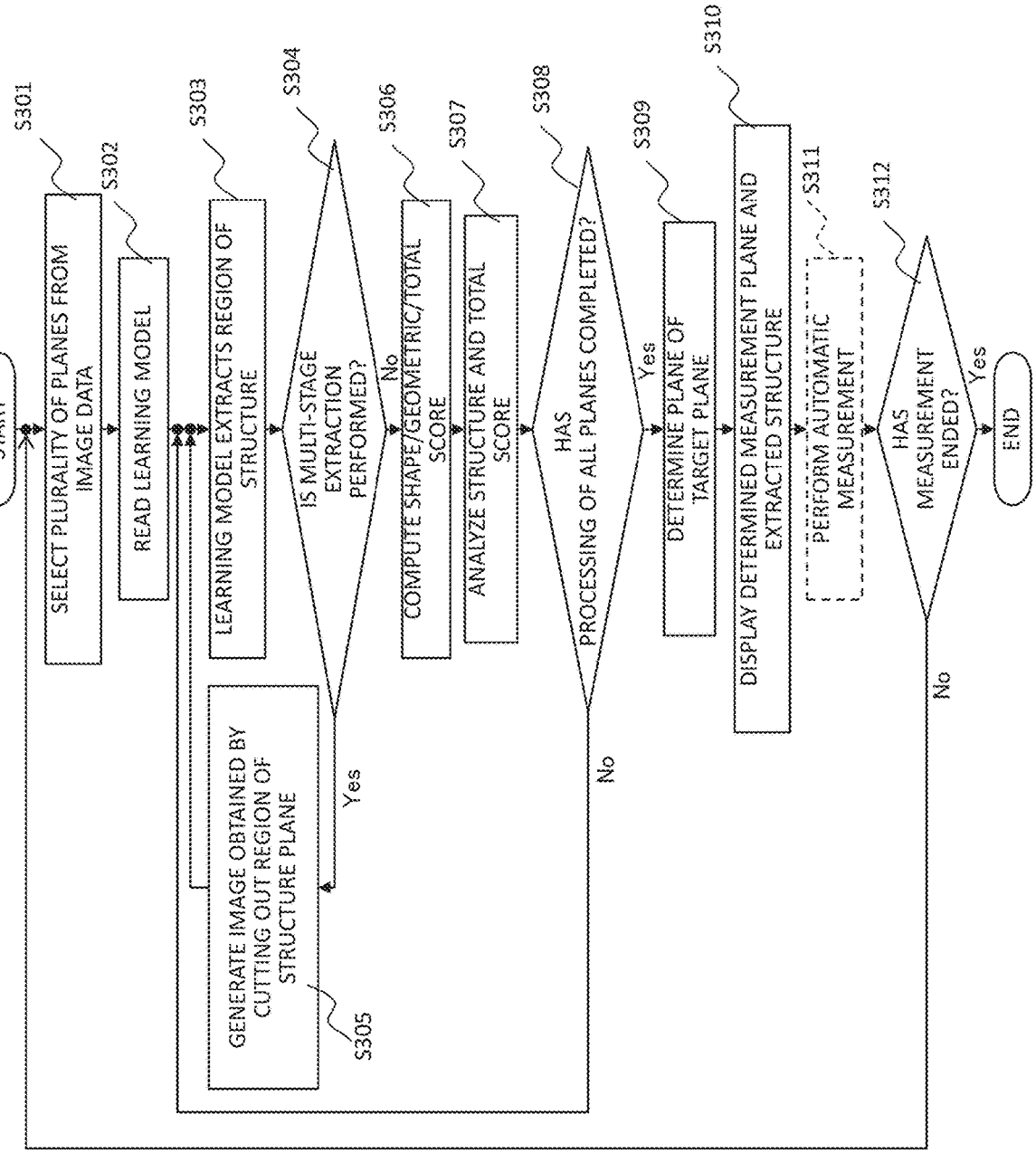
FIG. 3 is a flowchart illustrating a processing process of the image processing unit of the first embodiment.

Based on the above configuration, an operation of the medical imaging apparatus of the present embodiment, mainly a flow of processing of the image processing unit 200, will be described with reference to FIG. 3. Here, a case where imaging and image display are executed in parallel will be described as an example.

First, as a premise, for example, a type of the target plane to be identified by the user is selected via the operation input unit 330. The type of the target plane corresponds to a type depending on the difference in purpose such as whether the plane is for measurement or for determination of a direction in which the structure extends, a type depending on the measurement target (part, organ, or fetus), etc. Such input may be performed at the time of setting the imaging condition, or may be set by default when the imaging condition is set.

When the image processing unit 200 receives the 3D image data acquired by the imaging unit 100 or the image data 240 that is a time-series 2D image group, the plane selection unit 231 selects a plurality of planes from the image data 240 (S301). Here, when a direction of the target plane in the image space is known, the plane selection unit 231 selects a plurality of planes parallel to the direction and passes planes to the structure detection unit 232. For example, when a Z axis is set to a body axis direction and the target plane is known to be an XY plane, the XY plane is selected at a predetermined interval. In addition, when the image data 240 is volume data, the plane selection unit 231 may narrow down a region in which the target plane is present at high speed using spatial analysis by detecting a structure (tissue or part) included in the volume data. In addition, when the target plane is not determined to be a certain direction, the plane selection unit 231 selects planes in various directions from the image data 240. A plane selection scheme is preferably set to so-called "coarse to fine approach". In this approach, while repeating selection by the plane selection unit 231, detection of the structure and score by the structure detection unit 232, computation of the total score, etc. by the score computation unit 250, and analysis by the analysis unit 261, a region in which the plane is selected (referred to as a search region) is narrowed from a relatively wide region to a narrow region for each repetition. As the search region narrows, an interval between the selected planes may be narrowed and the number of plane angles may be increased.

The model introduction unit 270 reads a learning model from a storage unit 300 in accordance with the set target plane and stores the learning model in the model storage unit 271. The plane selection unit 231 passes the plane selected in step S301 to the structure detection unit 232. The model calling unit 272 calls the learning model to be applied from the model storage unit 271 and passes the learning model to the structure detection unit 232 (S302). The structure detection unit 232 inputs data of the selected plane to the learning model as an input image. At this time, when the size of the plane is larger than the size of the input image of the learning model, the plane is reduced so as to correspond to the input image size of the learning model. A region of the structure of the plane is extracted (detected) by the learning model, and a score indicating the reliability of detection of the region of the structure is output (S303). Subsequently, for multi-stage extraction, the structure detection unit 232 cuts out the region of the structure detected in step S303 from the plane and inputs the region again as an input image of the learning model (S304 and S305). At this time, when the image size of the cut region is smaller than the input image size, the region is enlarged and adjusted to the input image size. The learning model further detects a region of one or more structures included in the image of the cut region, and outputs a score indicating the reliability of detection (S303). In this way, a structure that is not extracted by applying the first learning model, such as a structure existing in the region of the structure extracted by the first extraction, can be extracted by the second extraction. Multi-stage extraction is repeated a predetermined number of times (number of levels) (S304).

The analyzed structure is output to the score computation unit 250 to compute a shape score, a geometric score, and a total score (S306). The shape score is computed based on the reliability score obtained in step S303 and the presence/absence of detection of the structure region, and the geometric score is computed based on a relative and geometric positional relation for two or more structure regions from anatomical knowledge. The total score is the sum of the shape score and the geometric score. Specific examples of a mathematical formula for computing the scores will be described in the second embodiment.

The analysis unit 261 analyzes structure extraction results of a plurality of planes and progresses of values of the shape score, the geometric score, and the total score to perform determination as to whether to end target plane search or determination of a plane group from which a structure is subsequently extracted (S307). The analysis unit 261 feeds back the analysis results to the plane selection unit step by step, and commands selection of a plane. The above steps S303 to S307 are successively performed for all the planes selected in step S301.

The plane determination unit 262 receives a result of the analysis unit 261, and finally determines that the plane having the highest total score is the image of the target plane (S309).

When the plane of the target plane is thus determined by the plane extraction unit 260, the display control unit 280 generates an image in which the extracted region of the structure is superimposed on the plane of the target plane, and causes the display unit 310 to display the image together with the values of the shape score, the geometric score, and the total score (S310). When the computation unit 210 has an automatic measurement function, predetermined measurement is performed using information on the region of the structure existing in the plane, and a result thereof is displayed on the display unit 310 via the display control unit 280 (S311). When there is a plurality of identification tasks (target planes) or when reprocessing is required due to user adjustment, the process returns to step S301, and S301 to S310 (or S311) are repeated (S312).

According to the present embodiment, when a learning model (discriminator) learned to detect a structure in a plane using learning data of multiple scales is used, and the learning model is applied to a tomographic image in multiple stages, it is possible to detect a region of the structure in a short time and with high accuracy. Further, by computing a geometric score and a total score based on anatomical knowledge, a plane having high suitability can be selected as an image of the target plane.

In addition, according to the present embodiment, since the learning model can be reduced, mounting on the imaging apparatus is facilitated, and the processing time by the learning model can be shortened. As a result, it is possible to shorten a time from imaging to display of the target plane or measurement using the target plane, and to enhance a real-time property.

In the first embodiment, when the image data 240 is time-series data, the analysis unit 261 analyzes the presence/absence of extraction of the structure on a time axis and a distribution of a score such as the total score in a time direction. When the image data 240 is 3D volume data, the analysis unit 261 analyzes integration of a region in which the structure is present in the space and a spatial distribution of the score such as the total score.

In addition, when it is desired to acquire an image of the target plane every predetermined time (time phase) while capturing time-series 2D image data, the image of the target plane can be automatically selected and displayed every predetermined time (time phase) by inputting the time-series 2D image data during imaging to the image processing unit 200 as the image data 240 in a predetermined time unit and performing the above-described processing.

In addition, when the target plane is not included in the time-series 2D image data, the target plane can be searched for by performing the processing by the image processing unit 200 in parallel while continuously performing imaging.

In the case of the time-series 2D image data, the plane selection unit 231 only needs to select an imaging plane (one-direction surface), and thus high-speed processing can be performed. Moreover, it is possible to select all the imaging planes captured at a predetermined interval.

The embodiment of the invention that can be applied regardless of the modality has been described above. In the following embodiments, an embodiment in which the invention is applied to an ultrasonic imaging apparatus will be described.

Second Embodiment

First, an ultrasonic diagnostic apparatus to which the invention is applied will be described with reference to FIG. 4.

(Configuration of Ultrasonic Diagnostic Apparatus)

A probe 410 is connected to an ultrasonic diagnostic apparatus 40 of the present embodiment. The ultrasonic diagnostic apparatus 40 includes a transmission beamformer 420, a digital/analog (D/A) converter 430, an A/D converter 440, a beamformer memory 450, a reception beamformer 460, an image processing unit 470, a display unit 310, and an operation input unit 330.

The probe 410 includes a plurality of ultrasonic elements arranged along a predetermined direction. Each of the ultrasonic elements uses, for example, a piezoelectric element made of ceramic, etc. The probe 410 is disposed in contact with a surface of a subject 101.

The transmission beamformer 420 outputs a transmission signal to at least some of the plurality of ultrasonic elements via the D/A converter 430, and transmits an ultrasonic wave from the ultrasonic elements. The D/A converter 430 D/A converts the transmission signal output from the transmission beamformer 420 to the ultrasonic element. The transmission beamformer 420 gives a delay time to the transmission signal output to each ultrasonic element so that the transmitted ultrasonic wave is focused at a predetermined depth. In this way, a transmission beam focused at a predetermined depth is generated.

In addition, the transmission beam is reflected in a process of propagating inside the subject 101, and a reflected wave (acoustic signal) arrives at the probe 410. The ultrasonic element of the probe 410 converts the arriving reflected wave into an electric signal again and generates a reception signal. The A/D converter 440 performs A/D conversion on the reception signal output by the ultrasonic element of the probe 410.

The beamformer memory 450 stores data indicating a delay amount for phasing the reception signal output from the ultrasonic element for each reception focus. The reception beamformer 460 receives the reception signal output from the ultrasonic element via the A/D converter 440 each time a transmission beam is transmitted, delays the reception signal by the delay amount read from the beamformer memory 450 to perform phasing, and then performs addition to generate a phased signal.

The image processing unit 470 generates an ultrasonic image (3D volume data or 2D tomographic image group) using the phased signal generated by the reception beamformer 460, and then automatically extracts an optimal plane for the target plane as described in the first embodiment. For this reason, the image processing unit 470 includes a data configuration unit 471 that generates ultrasonic image data using the phased signal generated by the reception beamformer 460, a data memory 472 that stores image data generated by the data configuration unit, a model introduction unit 270 that introduces a learning model, a structure extraction unit 230, a score computation unit 250, a plane extraction unit 260, an automatic measurement unit (computation unit) 210, and a plane adjustment unit 478 that receives user operation input. Further, although not illustrated, when Doppler imaging is performed, a Doppler processing unit that processes a Doppler signal may be provided.

The data configuration unit 471 is the same as that of a conventional ultrasonic imaging apparatus, and generates an ultrasonic image such as B mode or M mode.

Figure 4:
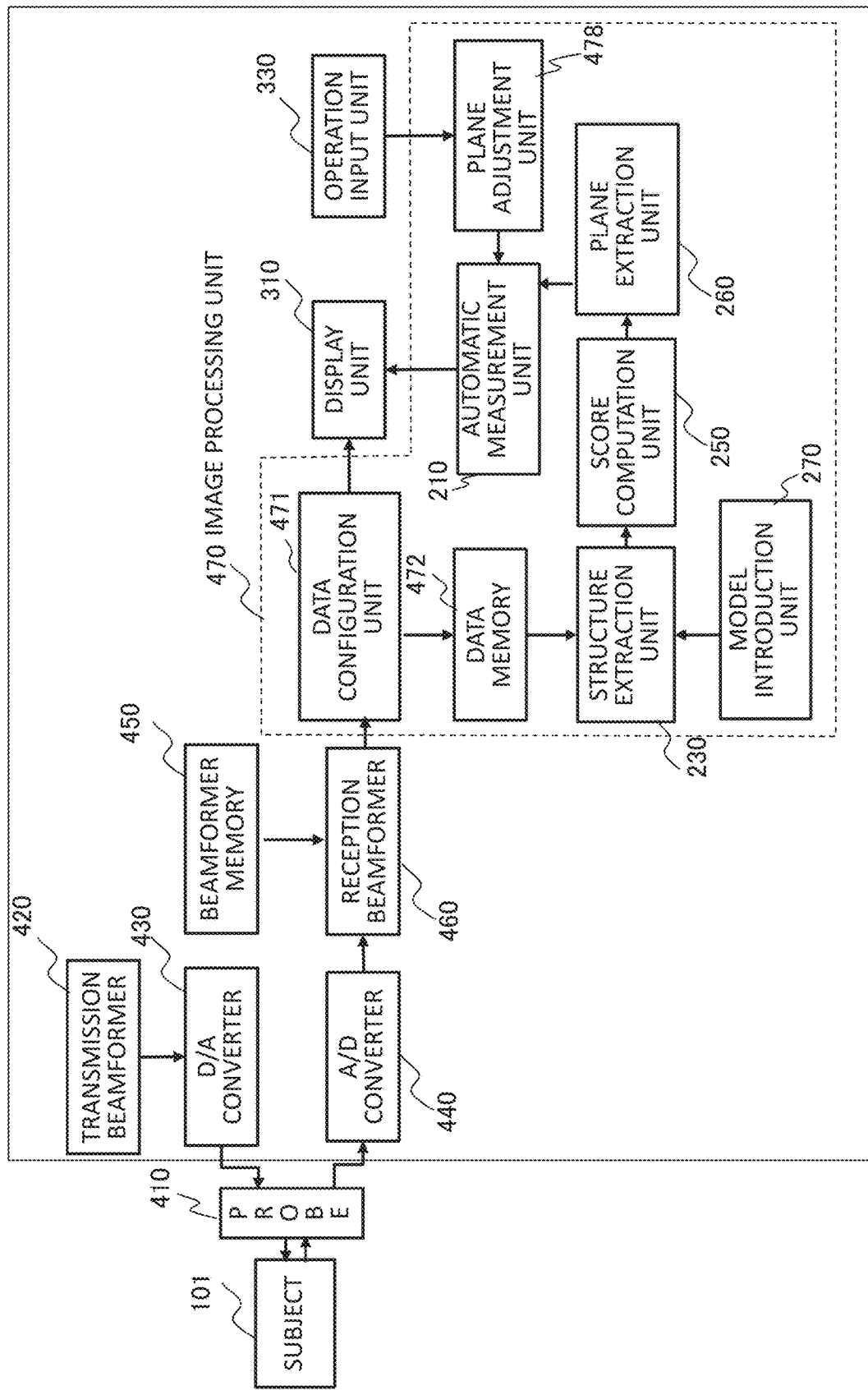
FIG. 4 is a block diagram illustrating a configuration of a medical imaging apparatus (ultrasonic diagnostic apparatus) of a second embodiment.

The model introduction unit 270 and the structure extraction unit 230 of FIG. 4 realize functions corresponding to the model introduction unit 270 and the structure extraction unit 230 of the first embodiment, respectively, and have similar configurations to those of the functional block diagram illustrated in FIG. 2. That is, the model introduction unit 270 includes a model storage unit 271 and a model calling unit 272, and the structure extraction unit 230 includes a plane selection unit (231), a structure detection unit (232), and a structure analysis unit (233). The score computation unit 250 includes a shape score computation unit (251), a geometric score computation unit (252), and a total score computation unit (253). The plane extraction unit 260 includes an analysis unit (261) and a plane determination unit (262).

In the following description, FIG. 2 will be used as appropriate, and a configuration and an operation similar to those of FIG. 2 will be briefly described. The plane selection unit 231 reads image data 240 (volume data or 2D plane group) of one subject in data stored in the data memory 472. In addition, the data read from the data memory 472 may be moving image data obtained by imaging a 2D plane or a dynamically updated image.

The structure detection unit 232 of the structure extraction unit 230 inputs the plane to the learning model introduced by the model introduction unit 270, and detects the region of the structure and the reliability score. The structure determination unit 233 removes erroneous detection and selects a structure having a high reliability score. The score computation unit 250 computes a shape score, a geometric score, and a total score based on the presence/absence of detection of the structure and the reliability score of each structure. The analysis unit 261 of the plane extraction unit 260 analyzes the structure and a progress of each score, and estimates whether to end search for the target plane, or a subsequent extracted plane group. The plane determination unit 262 of the plane extraction unit 260 determines a plane of the target plane based on an analysis result.

The automatic measurement unit 210 can be configured by software incorporated by inverse analysis of a feature map obtained by machine learning or a known automatic measurement algorithm using a region detection result of a structure, and performs measurement of a size, etc. of a predetermined part from a region of the structure of the plane of the target plane to compute a target measurement value from a value of the size, etc. using a predetermined algorithm.

The plane adjustment unit 478 receives correction or adjustment by the user via the operation input unit 330 for the plane of the target plane displayed on the display unit 310, and gives a command to change a plane position or reprocess automatic measurement associated therewith to the automatic measurement unit 210.

The display unit 310 displays the plane of the target plane extracted by the image processing unit 470, the region of the structure, the shape score/geometric score/total score, the automatically measured measurement value and measurement position, etc. The operation input unit 330 functions as an input device for receiving commands from the user such as position adjustment of the plane of the target plane extracted by user input, switching of the plane, switching of display/non-display, and adjustment of the measurement position. The image processing unit 470 performs a part of processing again according to a command received from the user, and updates the display result of the display unit 310.

(Description of Learning Model)

Next, a learning model 550 stored in the model storage unit 271 of the model introduction unit 270 will be described with reference to FIG. 5 to FIG. 8.

Figure 5:
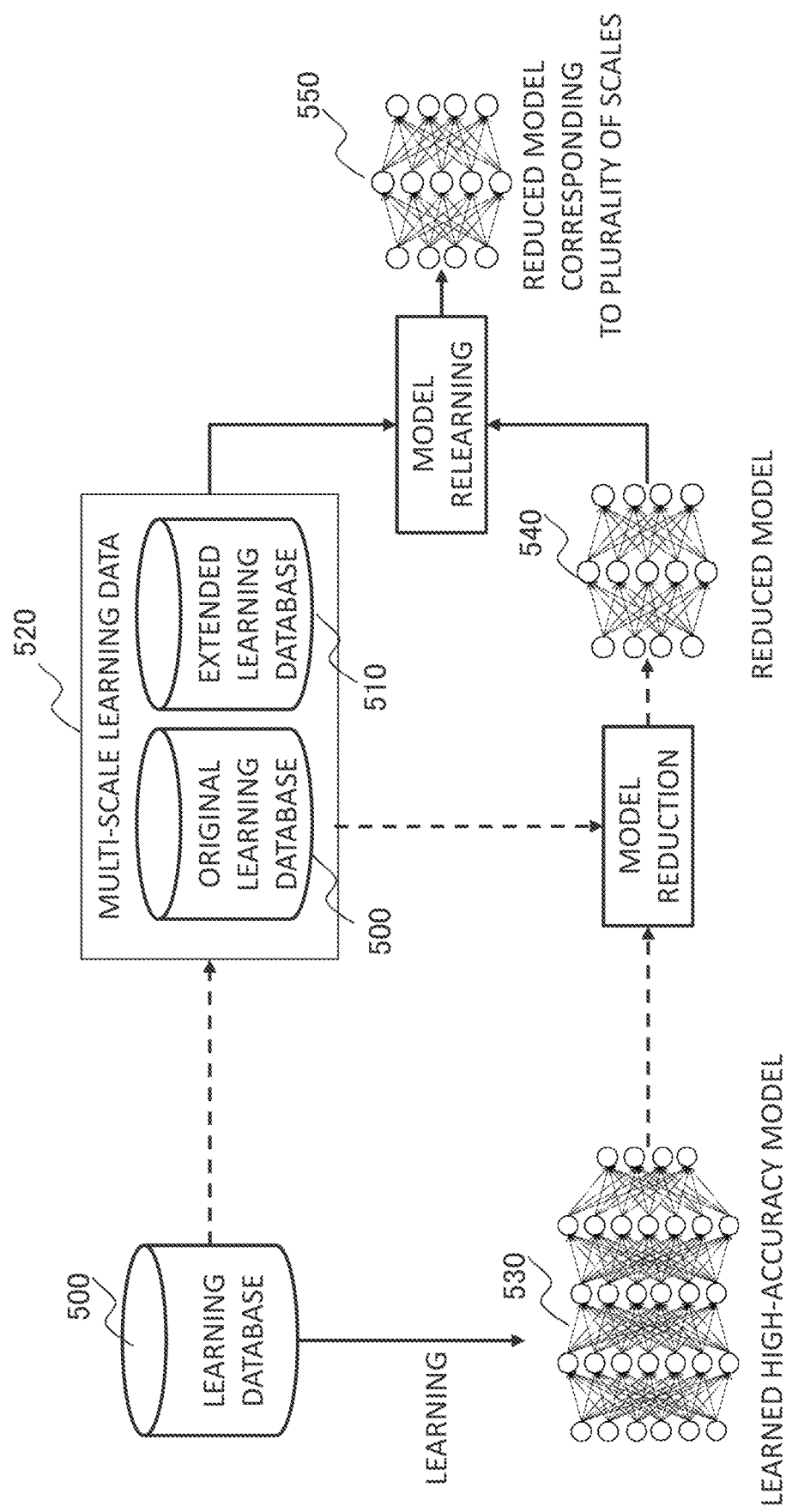
FIG. 5 is a diagram for description of an outline of a reduced model for learning using multi-scale learning data.
Figure 8:
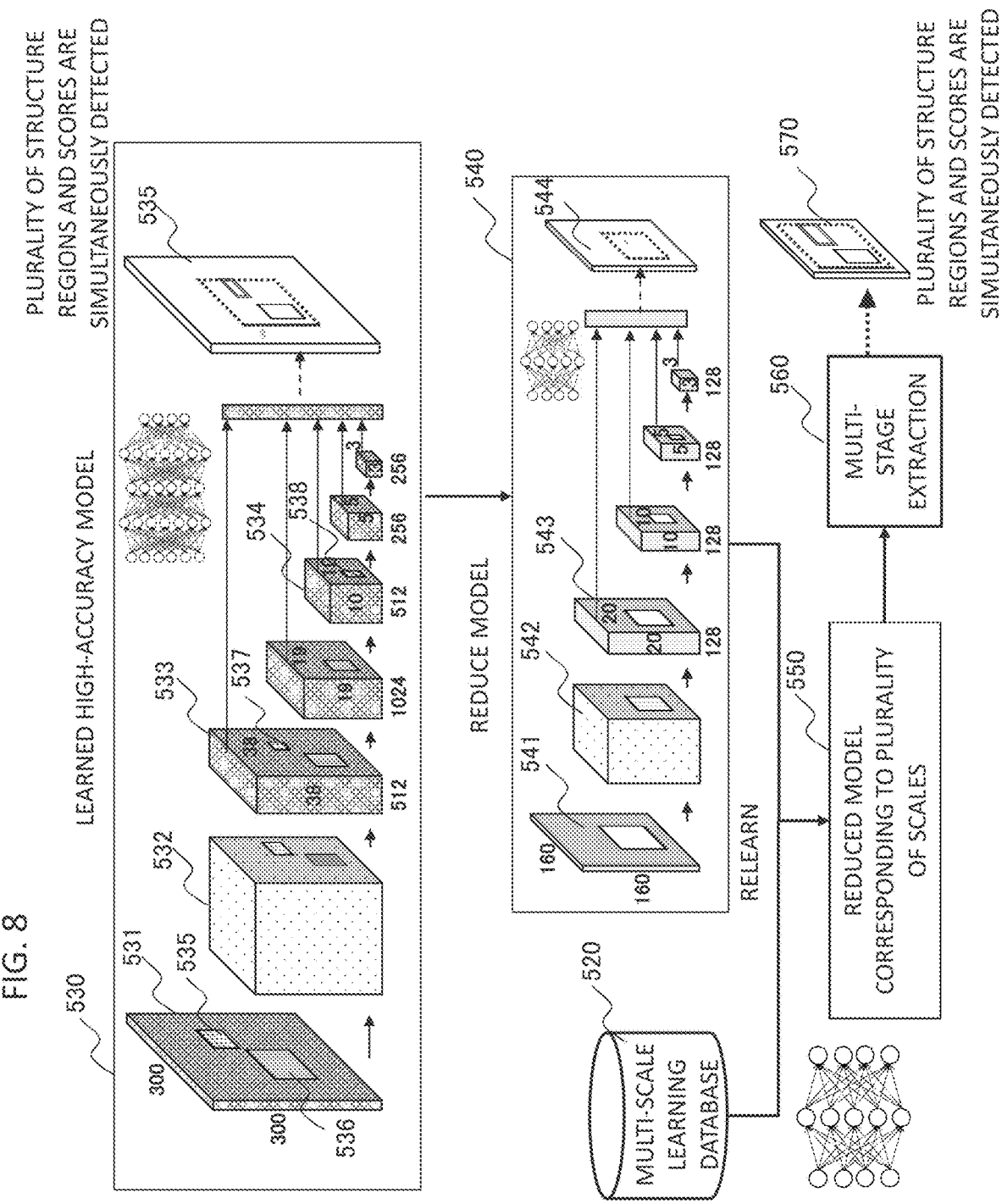
FIG. 8 is a diagram for description of a design concept of a reduced model.

The learning model 550 is a high-accuracy reduced model previously mounted in the ultrasonic diagnostic apparatus. As illustrated in FIG. 5 and FIG. 8, a configuration of the learning model 550 corresponds to a reduced model (540) obtained by analyzing a complex high-accuracy model (530) learned in an original learning database 500 and reducing the model to have a simple model configuration in accordance with analysis of a relative size of a region to be detected in learning data. As illustrated in FIG. 5, the reduced model 540 becomes a reduced model 550 corresponding to a plurality of scales by relearning a multi-scale learning data 520 including the original learning database 500 and an extended learning database 510.

Here, the original learning database 500 is a database of learning data, and a target plane for learning including an image of a predetermined structure imaged in advance for the target plane is used as the learning data. For example, the learning database 500 stores a large number of image data in advance, for example, a 3D image and 2D image of each growth week of the fetus, and region information of an internal target structure. The extended learning database 510 uses, as learning data, a region-of-interest plane for learning obtained by cutting out and expanding a partial region including a predetermined structure from the target plane for learning.

The model introduction unit 270 can be realized by a CPU or an image processing apparatus different from the ultrasonic imaging apparatus 40, and may be realized by a GPU in the apparatus when the ultrasonic imaging apparatus 40 is equipped with a GPU.

Figure 6:
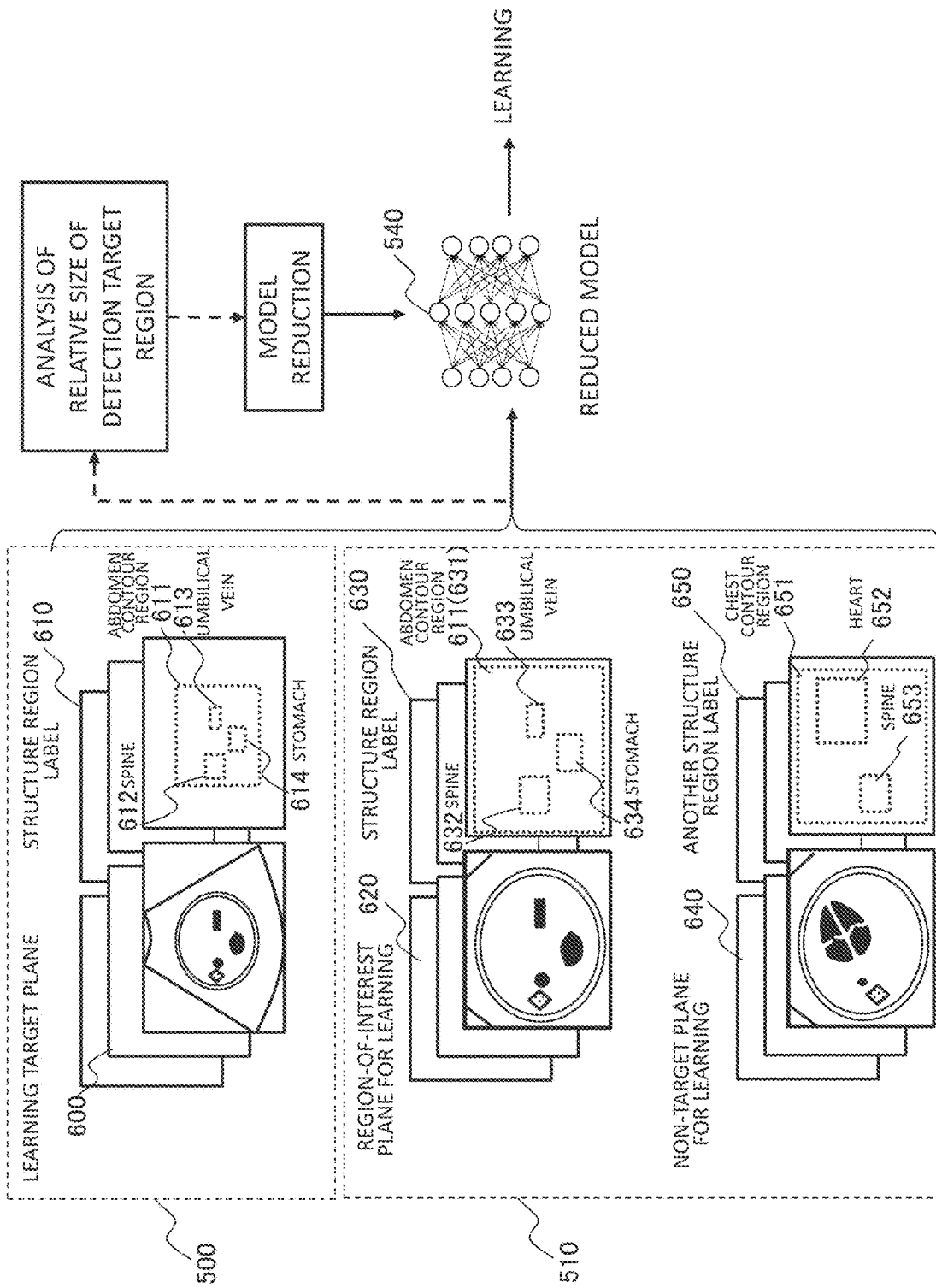
FIG. 6 is a diagram for description of an outline of a configuration of the multi-scale learning data.

Here, a configuration of the multi-scale learning data 520 will be described with reference to FIG. 6. FIG. 6 illustrates a case where the target plane is a fetal abdominal plane. As illustrated in FIG. 6, the multi-scale learning data includes the original learning database 500 and the extended learning database 510.

The original learning database 500 is configured by a set of a plurality of target plane for learnings 600 previously imaged for a target plane and a structure region label 610. The structure region label 610 corresponds to information in which information specifying a type of one or more structures included in the target plane 600 (for example, a name, an abdomen contour, a spine, an umbilical vein, etc.) is associated with position information of the region (for example, coordinates of four corners of the region), and corresponds to information in a form of a table, etc. Specifically, in the case of the abdomen, the structure region label 610 includes, as structures, position information of an abdomen contour region 611, a spine region 612, an umbilical vein region 613, and a stomach region 614 set for each of an abdomen contour and a spine, an umbilical vein, and a stomach inside the abdomen contour included in the target plane for learning 600. In an example of FIG. 6, as the regions 611 to 614 of the structures, rectangles having sizes corresponding to the structures are set. Thus, the structure region label 610 may correspond to a table in which coordinates of four corners of each region are associated with information (for example, name) specifying the type of structure as position information of the regions 611 to 614.

In addition, the extended learning database 510 includes a region-of-interest plane for learning 620 and a structure region label 630 thereof, and a non-target plane for learning 640 and a structure region label 650 thereof.

The region-of-interest plane 620 is learning data for making it possible to extract the internal structure of the region of interest on the enlarged scale image, and is obtained by cutting out the region of interest including the structures 611 to 614 set in the target plane 600 and enlarging the region of interest to the same image size as that of the target plane 600. For example, in the case of the abdomen illustrated in FIG. 6, the abdomen contour region 611 may be set as the region of interest, or the region of interest may be set outside the abdomen contour region 611. The region-of-interest plane 620 is included as a set with the structure region label 630 having region label information of the structure. The structure region label 630 has the same configuration as that of the structure region label 610, and is information in which type specifying information of one or more structures included in the region-of-interest plane 620 is associated with position information of a region thereof. For example, position information (coordinates, etc.) of an abdomen contour region 631, a spine region 632, an umbilical vein region 633, and a region 634 is included.

It is possible to prepare a plurality of types of region-of-interest planes 620 having different region-of-interest sizes, that is, having different enlargement rates. Alternatively, it is possible to have a cutout image of a structure inside the region of interest.

The non-target plane 640 is a plane of a part different from the target plane. The non-target plane 640 is included in the extended learning database 510 as a set together with another structure region label 650 indicating the internal structure and the position information of the regions 652 and 653. For example, when the target plane is the abdomen, a chest plane is a non-target plane, and a chest contour region 651 is similar to the abdominal outline region 611. However, the chest contour region 651 includes a heart region 652 that is clearly not a structure of the target plane. For this reason, when the structure extraction unit 230 detects (extracts) the heart region 652, a total score of the plane is reduced, and thus a possibility that the target plane is erroneously determined can be reduced.

Definitions of the target plane and the non-target plane vary depending on the target plane to be extracted. For example, the non-target plane 640 that is a chest plane is a target plane when the purpose is to extract a heart plane. Therefore, it is desirable to cause the learning model to learn planes having different enlargement rates as learning data for a plurality of types of target planes.

On the basis of the learning data, the learning model is reduced and the reduced model 540 is configured based on the analysis of the relative size of the detection target region and the analysis of the configuration of the complex high-accuracy model. A specific structure of the reduced machine learning model 540 will be described using a CNN corresponding to deep learning (DL) as an example.

FIG. 7 illustrates a basic configuration of the high-accuracy model 530 and a distribution of a size of the target structure. First, the basic configuration of the learning model 530 will be described. The learning model 530 has a convolution layer 532 for extracting a feature amount in a previous stage of the configuration with respect to an initial input image 531. The convolution layer 532 normally includes a plurality of layers, and the input image 531 is abstracted to some extent by the convolution layer 532. In the latter stage of the configuration, the size of the feature image is halved hierarchically as 38, 19, 10, 5, and 3 by convolution, and at the same time, the region size of the original image corresponding to one place in the layer increases by about 2 times. Then, by performing region estimation using the extracted feature amount of each level, it is possible to cope with extraction of structures having different level sizes. A front layer corresponds to region estimation of a small structure, and a back layer corresponds to region estimation of a large structure. As an example, a small structure 535 in the input image is estimated by a region candidate 537 in a front region extraction layer 533. A large structure 536 is estimated by a region candidate 538 in a latter half region extraction layer 534. In a final layer of the learning model, a region and an estimated value of each level are ranked, a highly reliable region candidate is selected, and a structure and a region 535 thereof are output in accordance with the input image 531.

In general, to achieve high accuracy, a complicated configuration such as the learning model 530 is required. Necessity is described according to the distribution of the size of the structure, taking an abdominal plane as an example. A graph 701 in FIG. 7 illustrates a size distribution of a structure for an original image of 300*300 pixels. A difference in size of internal structures such as the abdomen region and stomach is large and occupies about 10 to 150 pixels. First, necessity of a minimum input image size is verified. For an input image of 300*300 pixels, a size of a minimum extraction structure is 10, and a first region extraction layer is entered after constant convolution in a process of abstracting a feature of the convolution layer 532. Therefore, for example, when the input size is further reduced, a smaller structure (such as a partial umbilical vein, etc.) is previously mixed with a feature of another region before entering the region extraction layer 533, and the region is not estimated. Next, the necessity of the region extraction layer is verified. When the region size of the structure to be detected is greatly different and increases by about 2 times between 10 and 150 pixels, about five levels of 10, 19, 38, 75, and 150 pixels are obtained as illustrated in the graph 701. Therefore, the region extraction layer needs to have at least five layers to hierarchically correspond to detection of structures having different sizes. Furthermore, a difference in shape in an actual captured image is large, and the number of channels in each layer is large in order to cope with diversity. As described above, in general, in order to maintain high accuracy due to the distribution feature of the detection target such as the graph 701, a complicated layer configuration such as the learning model 530 is required.

However, the learning model takes processing time as the layer configuration becomes complicated. In an ultrasonic diagnostic apparatus, etc., immediate responsiveness is required. Therefore, a distribution of the relative size of the structure is focused, and a method is examined to reduce the learning model based on analysis of a characteristic thereof. First, a possibility of reducing the input image is examined. When the input image can be reduced, an overall calculation amount can be greatly reduced. Even though it is difficult to reduce the input size in order to simultaneously detect from a small structure to a large structure from an original image, the input size can be reduced if the structures are detected in stages. In a distribution 701, an abdomen region (AC_ROI) is a structure that is large and significantly easy to find with respect to the original image. Even when the input image is slightly reduced, since a relative size of AC_ROI is large, detection is easy. In this regard, a graph 702 shows a distribution of relative sizes of other structures when a region-of-interest plane is cut out centering on the abdomen region (AC_ROI) and the size of the AC_ROI is normalized based on 150 pixels. When the sizes of the other structures are intensively distributed from 20 to 60 pixels with respect to the AC_ROI size of 150 pixels, and increased by about two times between 20 to 150 pixels including the AC_ROI, about four levels of 10, 20, 40, 80, and 160 pixels are obtained as illustrated in the graph 702. In addition, for a region-of-interest plane of 160*160 pixels, even a small structure has a size that is relatively easy to recognize (20 pixels), the region remains even after passing through the convolutional layer, and region estimation is easy. Therefore, when a problem is divided to extract a region of interest (AC_ROI) from the original image and further extract a detailed structure from the AC_ROI by analysis, it is possible to cope with a learning model having a small input size. By reducing the input size, the total number of convolution layers is reduced, and the amount of calculation from the input to each layer is reduced. Further, as shown in a distribution diagram of the graph 702, after normalizing data by the AC_ROI size, the data becomes more uniform and can be handled with a small number of region extraction layers and a channel width. Further, in a detailed design, a parameter of the estimation region can be adjusted in accordance with the size distribution of the relatively small structure on the front side of the region extraction layer. In this way, a suitable reduced model can be designed according to the analysis of the size distribution of the detection target.

FIG. 8 illustrates an example of a layer configuration change before and after the learning model is reduced and a flow of relearning. In the above description, taking an abdomen plane as an example, a possibility of model reduction has been described by relative analysis of structures. Compared to the learning model 530 before reduction, the reduced learning model 540 reduces the input image size from 300*300 pixels to 160*160 pixels, so that a feature convolution layer 542 becomes relatively light. The region extraction layer has been reduced from the conventional 5 layers to 4 layers, and the size of each layer has been reduced. In addition, this scheme makes it possible to make the relative size of the same type of structure relative to AC_ROI more uniform, and thus the number of channels in each layer of the structure can be reduced. In the present embodiment, it has been confirmed that the detection accuracy is ensured even when the number of channels in the layer is reduced from 512 or 1024 to 128 by parameter adjustment. As a result, the overall size of the learning model is reduced to about one-tenth of the conventional model, and the processing speed can be increased to be 10 times faster than the conventional model. The layer configuration illustrated in FIG. 8 is an example of reduction according to data analysis, and is not necessarily limited to all the illustrated layer configurations.

Since the high-accuracy learning model 530 has high detection accuracy for structures of different sizes, the image size of the input image 531 is large, the number of levels is large, and the channel width that is the number of output dimensions of convolution in the level is large. For this reason, the size of the entire learning model is large and processing time is required. A model capable of high-speed processing with as little memory as possible while having high accuracy in mounting the apparatus is desirable. Therefore, in the present embodiment, the learning model is reduced in order to solve the problem of mounting the machine learning model on an actual apparatus. Specifically, the learning model 530 is analyzed, and at least one of the input image size, the number of levels, and the channel width of the learning model is reduced while maintaining the basic function. Here, the input image size, the number of levels, and the channel width of the learning model are all reduced. At the time of reduction, the size and the number of levels of the input image, and the corresponding region size inside each layer are designed based on the distribution analysis of the relative sizes of the structure to be detected, the target plane, and the region-of-interest plane. By analyzing the distribution of relative sizes, the number and size of convolutional layers corresponding to different sizes can be set appropriately, and the required minimum input size can be designed small. In addition, the number of channels is increased for the detection layer corresponding to a place where the distribution is concentrated so as to correspond to diversity of inputs. A small number of channels correspond to a place where the distribution is small. As a result, a simple reduced model 540 having a reduced input image 541, a shallow feature extraction layer 542, a small region extraction level 543, and a structure output layer 544 is obtained. In addition, a region estimation parameter inside the region extraction layer 543 can be adjusted according to a relative distribution of structures. The reduced model 550 is a reduced model corresponding to multiple scales that can extract structures of different sizes while having a simple configuration by relearning using the multi-scale learning data 520. In addition, since an attention region can be narrowed down using a combination with multi-stage extraction 560, even a structure having a small scale in a plane can be extracted by generating a plane of a scale obtained by cutting out and enlarging a partial region of the plane and applying the reduced model 550 thereto again. Further, in a cut image of the region of interest which has been narrowed down, since the internal structure is anatomically uniform to some extent, it is one of the factors that can be dealt with by the small number of layers and the number of channels of the reduced model. Therefore, it is possible to acquire a learning model that has an accuracy equivalent to or higher than that of the high-accuracy learning model 530 and has a short processing time while being the reduced model 550.

(Description of Multi-Stage Extraction)

Figure 9:
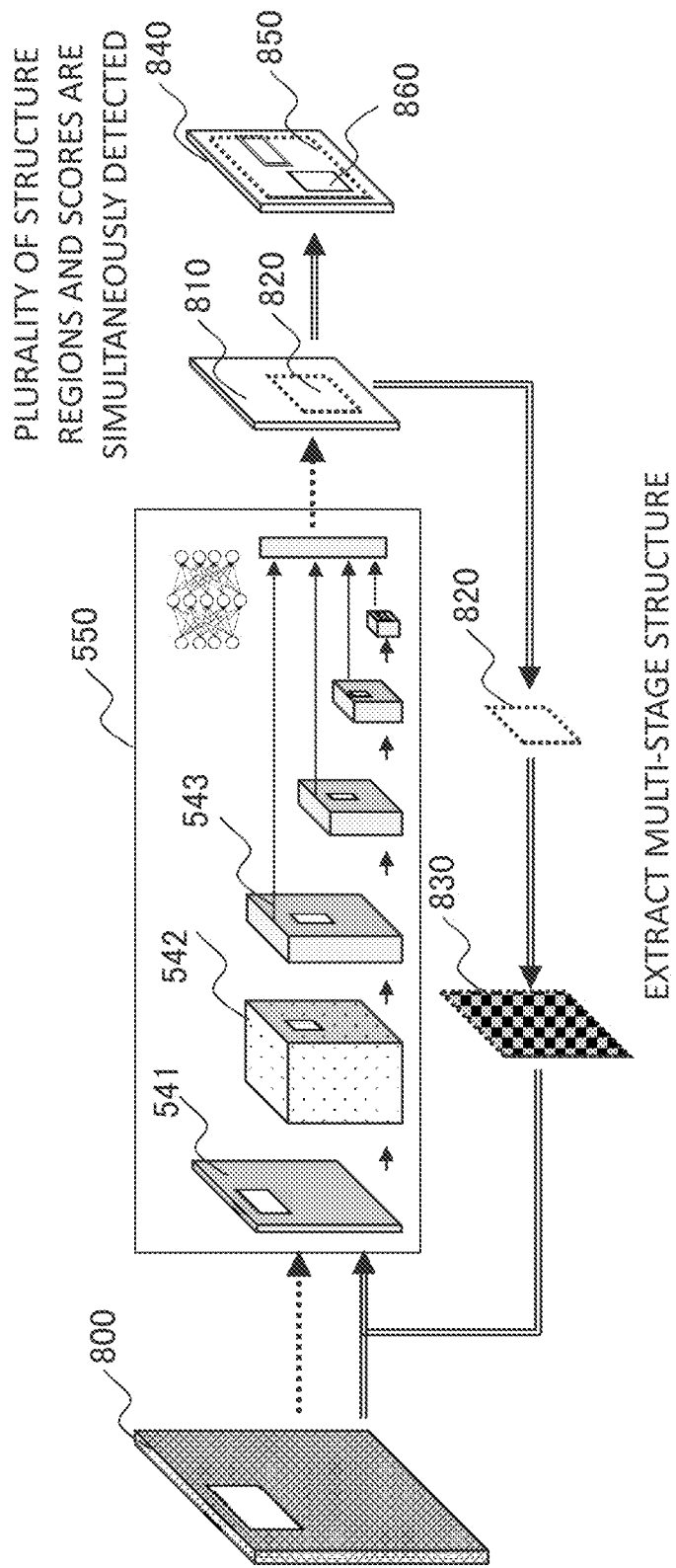
FIG. 9 is a diagram for description of multi-stage structure extraction using the reduced model.

Details of the multi-stage extraction will be further described with reference to FIG. 9. First, the structure detection unit 232 resizes (reduces) the plane 800 to be detected to the size of the input image 541 of the learned reduced model 550 corresponding to a plurality of scales and inputs the image to the reduced model 550. As a result, a first-stage identification (detection) result 810 is obtained from the reduced model 550.

Since the reduced model 550 has a small image size of the input image 541, in processing of a first stage of the reduced model 550, a region 820 of a relatively large structure in the plane 800 (for example, in the case of the abdomen, the abdomen contour region) is detected, and a small structure inside a large structure may not be detected. Therefore, the structure detection unit 232 generates a new input image obtained by cutting out a region 830 in the plane 800 corresponding to the detected large structure region 820 from the plane 800. The structure detection unit 232 inputs the cut-out input image as the input image 541 to the reduced model 550, and performs an identification process again. However, when the cut-out input image is smaller than the input image 541 of the reduced model 550, the input image is enlarged and input. As a result, a second-stage detection result 840 is obtained from the reduced model 550.

In the second-stage detection result 840, since the attention region is narrowed down, not only a large structure region 850 corresponding to the first-stage structure region 820 but also a small structure region 860 inside thereof is detected. From the reduced model 550, along with the detection of the region of the structure, a reliability score for detection of each structure is output.

Here, as an example, the structure extraction is performed twice for the abdomen region. However, other stage identification may be automatically adjusted or manually set three times or more according to the size and depth of the target structure to be extracted.

(Description of Score Computation Unit 250)

Details of the score computation unit 250 will be described with reference to the abdomen plane of FIG. 10. As a result of the structure detection, as in 910, information (name) specifying the type of each structure, structure regions 911 to 913, and reliability scores $S_1$ to $S_4$ of the detected structure are obtained. In an example of FIG. 10, an abdomen contour region 911 and a score $S_1$, a spine region 912 and a score $S_2$, an umbilical vein region 913 and a score S3, and a stomach region 914 and a score $S_4$ are detected.

Figure 10:
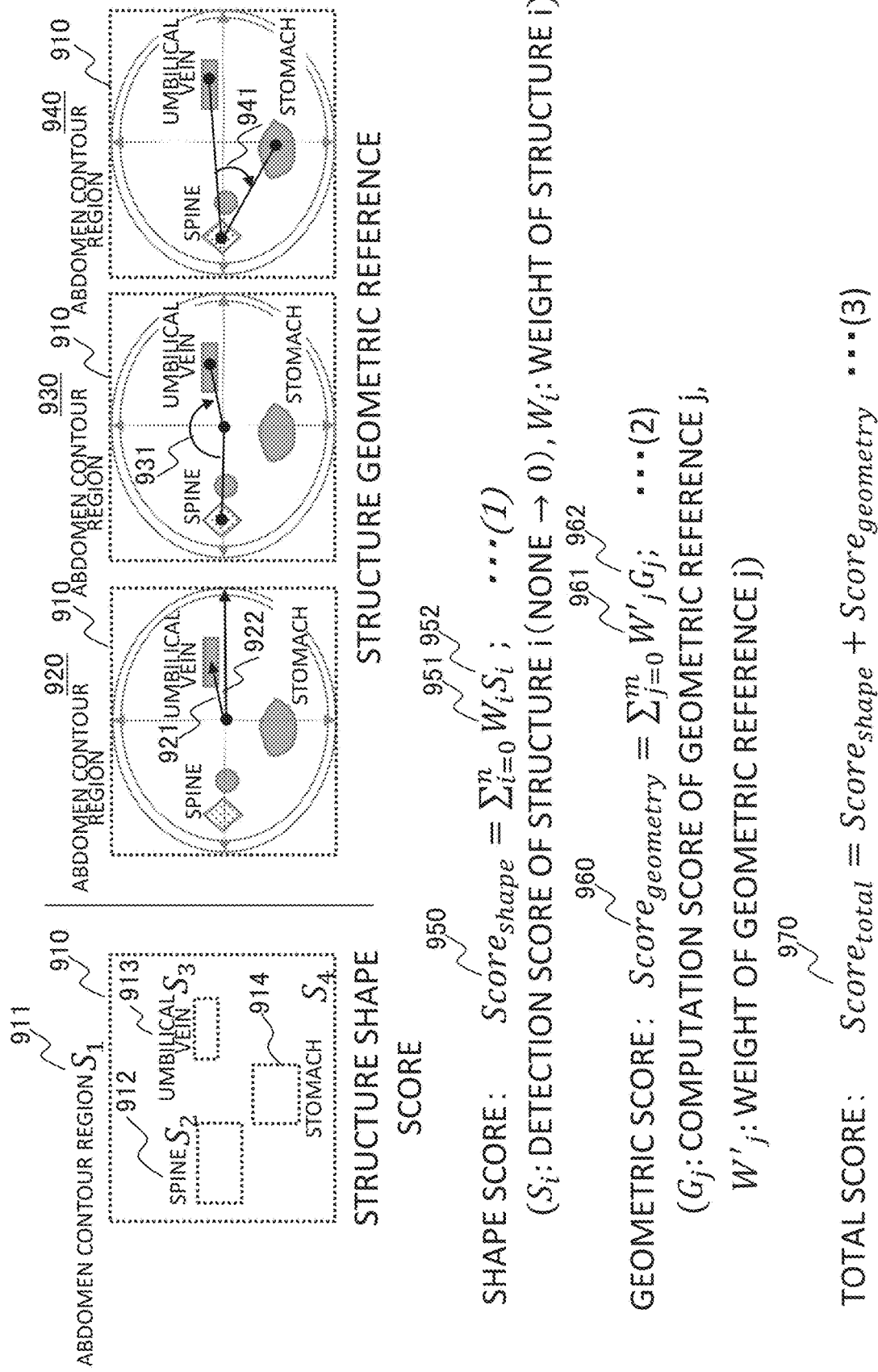
FIG. 10 is a diagram for description of a structure of an abdomen plane and a score calculated by a score computation unit.

The shape score computation unit 251 of the score computation unit 250 computes a shape score 950 according to predetermined Equation (1) shown in FIG. 10 weighted by a weight ($W_i$) 952 according to an importance based on the presence/absence of detection of each structure and a reliability score 952. In addition, the weight is determined in advance for each target plane and structure. In addition, a negative weight ($W_i$) is set for a structure that is clearly not included in the target plane (for example, a heart structure when attempting to detect the abdomen target plane). In this way, since the shape score 950 of the plane including the structure not included in the target plane can be reduced, it is possible to prevent the non-target plane from being selected as the target plane.

The geometric score computation unit 252 of the score computation unit 250 computes a predetermined geometric angle or distance as a geometric reference computation score $G_j$ 961 according to a positional relationship between the detected regions of the plurality of structures. Then, the geometric score 960 is computed according to predetermined Equation (2) shown in FIG. 10 in which the computed score $G_j$ is weighted by a weight ($W_j$) 962. Taking the abdomen as an example, a distance 921 between a center of the abdomen contour region 910 and the umbilical vein region 913 and a distance 922 between the center and the abdomen contour region 820 are computed as one reference 920 to obtain a ratio, and $G_j$ 961 is scored according to whether an appropriate proportional range set in advance is obtained. Further, for example, as a reference 930, an angle 931 formed by the spine region 912 and the umbilical vein region 913 around the center of the abdomen contour region 910 may be set as $G_j$ 961. Furthermore, as a reference 940, an angle 941 formed by the umbilical vein region 913 and the stomach region 914 around the spine region 912 may be used as $G_j$ 961.

The total score computation unit 253 finally obtains a total score 970 from Equation (3) of FIG. 10 by combining the shape score and the geometric score.

(Description of Automatic Measurement Unit 210)

A specific example of automatic measurement will be described by taking fetal weight measurement and cardiac measurement as examples. In general, in fetal weight measurement, as illustrated in FIGS. 11A to 11D, with respect to a fetal structure to be measured, a biparietal diameter (BPD) is measured from a fetal head plane 1010, an abdominal circumference (AC) is measured from an abdomen plane 1020, a femur length (FL) is measured from a femoral plane 1030, the fetal weight is estimated based on those measurement values, and it is determined whether the fetus is favorably growing when compared to a growth curve according to the number of weeks.

Figure 11A:
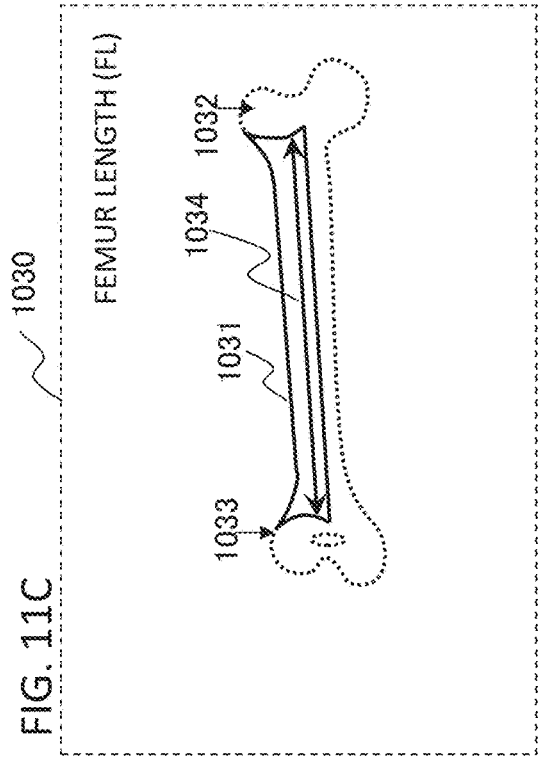
FIGS. 11A to 11D are diagrams illustrating measurement positions in a fetal target plane.

In the fetal head plane, as illustrated in FIG. 11A, it is recommended by a guideline that a plane having structural features of a skull 1010, a midline 1012, a transparent septum 1013, and a corpora quadrigemina tank 1014 is used as the target plane. The measurement object varies depending on the country. For example, in general, in Japan, a BPD 1015 is measured from the fetal head plane. In the West, an occipitofrontal diameter (OFD) 1016 and a head circumference (HC) 1017 are measured. A target measurement position may be set before preset of the apparatus or measurement.

In the extracted plane of the target plane, the score computation unit 250 (FIG. 4) performs predetermined measurement by an automatic measurement technology such as the technology described in International Patent Application No. 2016/190256, for example. In this technology, for a head, an ellipse corresponding to the head is computed from a characteristic of the tomographic image, and the diameter of the head is computed.

Figure 11B:
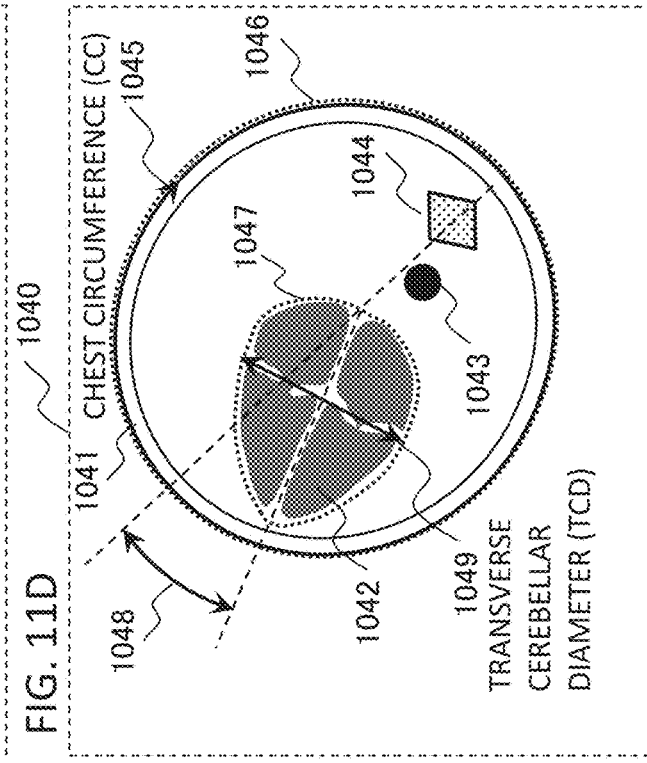

In the fetal abdomen plane, as illustrated in FIG. 11B, it is recommended by a guideline that a plane having structural features such as an abdominal wall 1021, an umbilical vein 1022, a stomach 1023, an abdominal aorta 1024, and a spine 1025 is used as the target plane. In this target plane, in general, the AC 1026 is measured. Depending on the region, an anterior posterior thoracic diameter (APTD) 1027 and a transverse thoracic diameter (TTD) 1208 may be measured. A target measurement position may be set before preset of the apparatus or measurement. A measurement scheme is the same as that for the head.

Figure 11C:
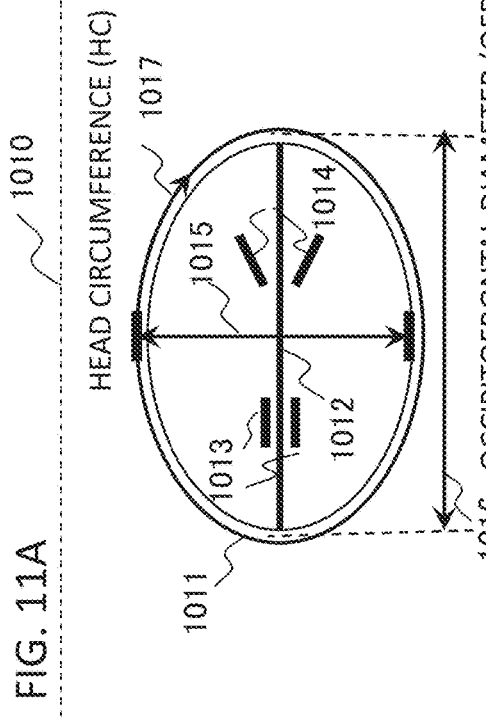

As illustrated in FIG. 11C, in a fetal femur plane, a plane having structural features such as a femur 1031, a distal end 1032 which is both ends of the femur, and a proximal end 1033 is recommended by a guideline. In this target plane, an FL 1034 is measured.

The score computation unit 250 computes an estimated weight according to, for example, the following equation using each of measurement values (BPD, AC, and FL) measured in these three planes.

$$\text{Estimated weight} = a \times (BPD)^3 + b \times (AC)^2 \times (FL)$$

(a and b are coefficients obtained from experience values. For example, a=1.07 and b=0.30.)

The automatic measurement unit 210 causes the display unit 310 to display the measurement value of each part and the computed estimated weight.

Figure 11D:
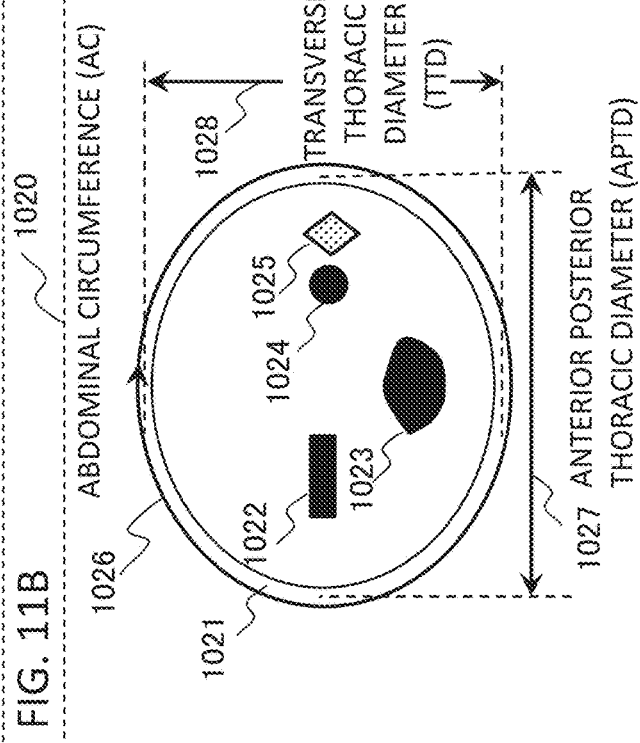

In the fetal heart plane, as illustrated in FIG. 11D, it is recommended by a guideline that a plane having structural features such as a chest wall 1041, a heart 1042 depicting four chambers of the heart, a descending aorta 1043, and a spine 1044 is used as the target plane. A great deal of information is contained in a cardiac four-chamber plane. In general, a chest circumference (CC) 1045, a ribcage area 1046, a heart area 1047, a cardiac axis 1048, a transverse cerebellar diameter (TCD) 1049, etc. are measured. In addition, a cardiac thorax area ratio (CTAR), which is a ratio of the heart area to the thorax area, is calculated. A target measurement position may be set before preset of the apparatus or measurement.

A description has been given that the AC target plane, the BPD target plane, the FL target plane, and the target plane of the cardiac four-chamber plane necessary for fetal weight measurement are extracted to perform automatic measurement. However, the present embodiment is characterized in that the reduced learning model 550 is used to identify a structure and extract an image of a target plane, and is not limited to the automatic measurement described above. In addition to the 4CV plane of the heart (cardiac four-chamber plane) for examining the fetal heart function, the present invention is applicable to extraction of a three vessel view (3VV) plane, a left ventricular outflow tract plane, a right ventricular outflow tract plane, and an aortic arch plane, and automatic extraction of a target plane of an amniotic fluid pocket to measure fetal amniotic fluid volume. Further, the present embodiment can be applied to automatic extraction of a standard plane necessary for measurement and observation of an adult heart and circulatory organs as well as a fetus.

(Example of Detected Structure)

Based on the configuration of the ultrasonic imaging apparatus 40 and the characteristic of the target plane of FIG. 12, an example of a structure that is detected (extracted) by the structure detection unit of the present embodiment will be described. Here, as an example, structures of a fetal measurement abdominal plane, a head plane, a femur plane, and a chest plane will be described as examples.

Figure 12:
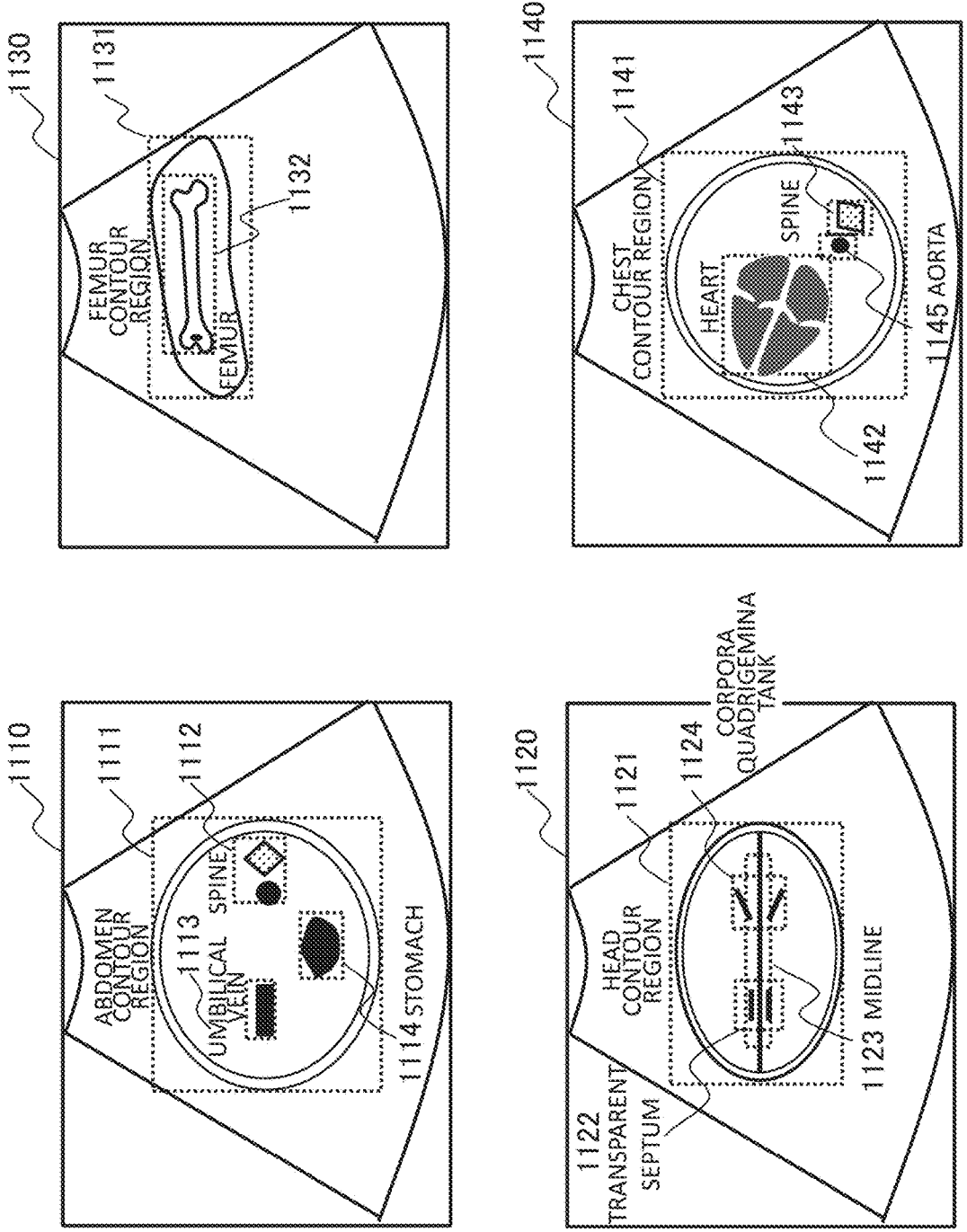
FIG. 12 is a diagram illustrating an example of a target plane.

As illustrated in FIG. 12, when a fetal measurement abdominal plane 1110 is a target plane, a abdomen contour region 1111, a spine 1112, an umbilical vein 1113, and a stomach 1114 can be detected as structures by the learning model 550.

When a head plane 1120 is a target plane, a head contour region 1121, a transparent septum 1122, a midline 1123, and a corpora quadrigemina tank 1124 can be detected by the learning model 550.

When a femur plane 1130 is a target plane, a femur contour region 1131 and a femur 1132 can be detected.

When a chest plane 1140 is a target plane, a chest contour region 1141, a heart region 1142, and a spine 1143 can be detected.

(Processing to Extract Image of Target Plane from 2D Planes Captured Continuously)

A description will be given of processing from acquisition of data to generation of a plane group and extraction of an image of a target plane when image data is a continuous 2D plane on the time axis with reference to FIG. 13 and FIG. 5.

Figure 15:
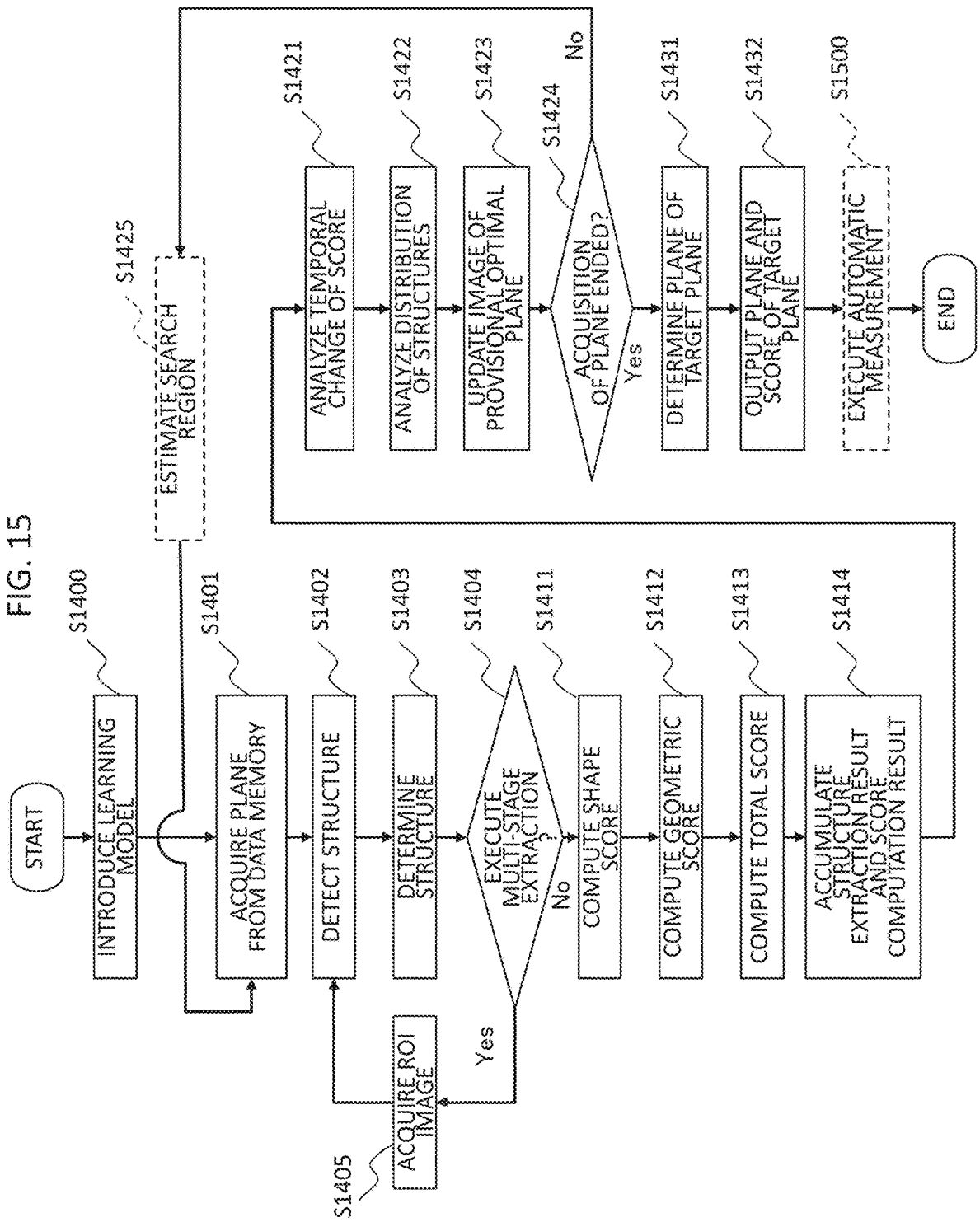
FIG. 15 is a flowchart illustrating a plane extraction processing step by structure extraction according to the second embodiment.

As in a processing flow illustrated in FIG. 15, in the present embodiment, a 2D plane 1201 continuously imaged in time is captured while moving the 1D probe 410 with respect to a fetus 101 corresponding to the subject and accumulated in the data memory 472. The model introduction unit 270 introduces the learning model 550 corresponding to the target plane set by default or the user from the model storage unit 271 and passes the learning model 550 to the structure detection unit 232 (S1400). The plane selection unit 231 samples the plane data 1201 called from the data memory 472 on the time axis, and generates a plane group 1202 to be processed (S1401). That is, a search region on the time axis is determined, and a frame image on the time axis is selected. For the determination of the search region, a coarse-fine approach may be taken. In addition, regarding a plane captured in real time, a plane that is continuously input is processed without change.

The structure extraction unit 230 reduces the plane to be processed to the size of the input image and inputs the plane to the learning model 550 received from the model introduction unit 270. In this way, the region and reliability score of the structure are detected (S1402). The structure extraction unit 230 determines the structure based on the detected region and reliability score of the structure, selects a structure having high reliability, and removes an erroneously detected structure (S1403). In addition, it is determined whether to process multi-stage extraction according to the level of the structure to be detected (S1404). At the time of performing multi-stage extraction, among the regions of the structure detected in step S1402, a region of a predetermined large structure or a structure designated by the user is used as an ROI, and an image obtained by cutting out an image of a region corresponding to the ROI in the plane to be processed is generated (S1405). Then, the process returns to step S1402, and the structure extraction unit 230 enlarges the cut-out image to the size of the input image and inputs the image. In this way, a region and a reliability score of a small structure included in the cut-out image are detected. The structure extraction unit 230 repeats the extraction in steps S1402 to S1405 a predetermined number of times.

When the multi-stage extraction ends in step S1404, an integration result (image or position information) 1203 is generated by integrating the structure detected in multiple stages and the score extraction result. Based on the integration result 1203, the score computation unit 250 computes a shape score and a geometric score representing suitability of the plane (S1411 and S1412). Furthermore, the score computation unit 250 computes a total score (S1413). The structure extraction unit 230 and the score computation unit 250 accumulate the structure extraction result and the score computation result in a memory (not illustrated) (S1414).

The analysis unit 261 of the plane extraction unit 260 analyzes a temporal change 1204 of the total score computed by the score computation unit 250 (S1421), further analyzes the distribution of the detected structures (S1422), and updates a provisional optimal plane up to the present time (S1423). For example, the analysis unit 261 selects a plane having a highest total score and having a structure distribution within a predetermined range as the optimal plane. It is determined whether an image of a target plane that is sufficiently suitable for measurement has been found, or whether an end of search has been commanded by a user operation (S1424).

When acquisition of the plane has not been ended, the analysis unit 261 estimates a search region for subsequent plane to be processed based on an analysis result and an input format (S1425), and outputs the estimated search region to the plane selection unit 231. Accordingly, the process starts again from the acquisition of the plane to be processed in step S1401.

When the analysis unit 261 determines that the plane acquisition has ended, the plane determination unit 262 determines that the provisional optimal plane is a plane 1205 of the target plane (S1431). The plane extraction unit 260 outputs the extracted plane 1205, a structure region extraction result, and an evaluation score 1204 as a plane extraction result (S1432). The automatic measurement unit 210 performs automatic measurement based on a result of extracting the region of the target plane as necessary (S1500).

When imaging is continuously performed in parallel with this image processing, a plane called from the data memory may be updated by an imaging operation of the user at the time.

Figure 13:
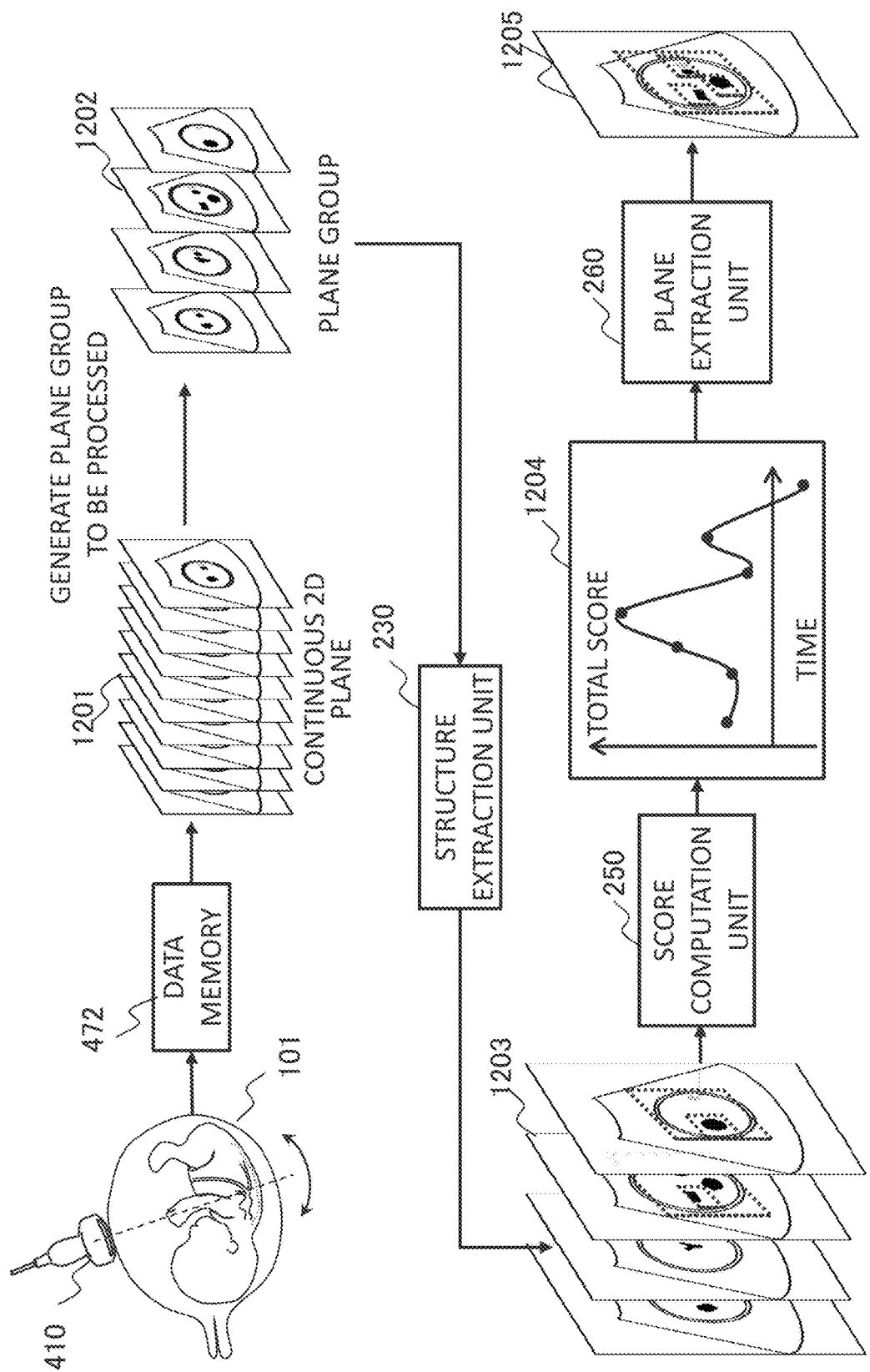
FIG. 13 is a diagram for describing that a plane is extracted by performing structure extraction and score computation from a time-series 2D image of a second embodiment.

Even though FIG. 13 illustrates a case where the 2D plane data is called from the data memory 472, read data may be 3D volume data acquired by one scan, or a plurality of pieces of 3D volume data continuously scanned in a 4D mode. When the input data is a plurality of pieces of 3D volume data, after extracting one plane from one piece of volume data, the volume is updated and the plane is extracted. Finally, one plane is determined from candidate planes extracted from the plurality of pieces of volume data.

(Processing to Extract Image of Target Plane from 3D Volume Data)

Figure 14:
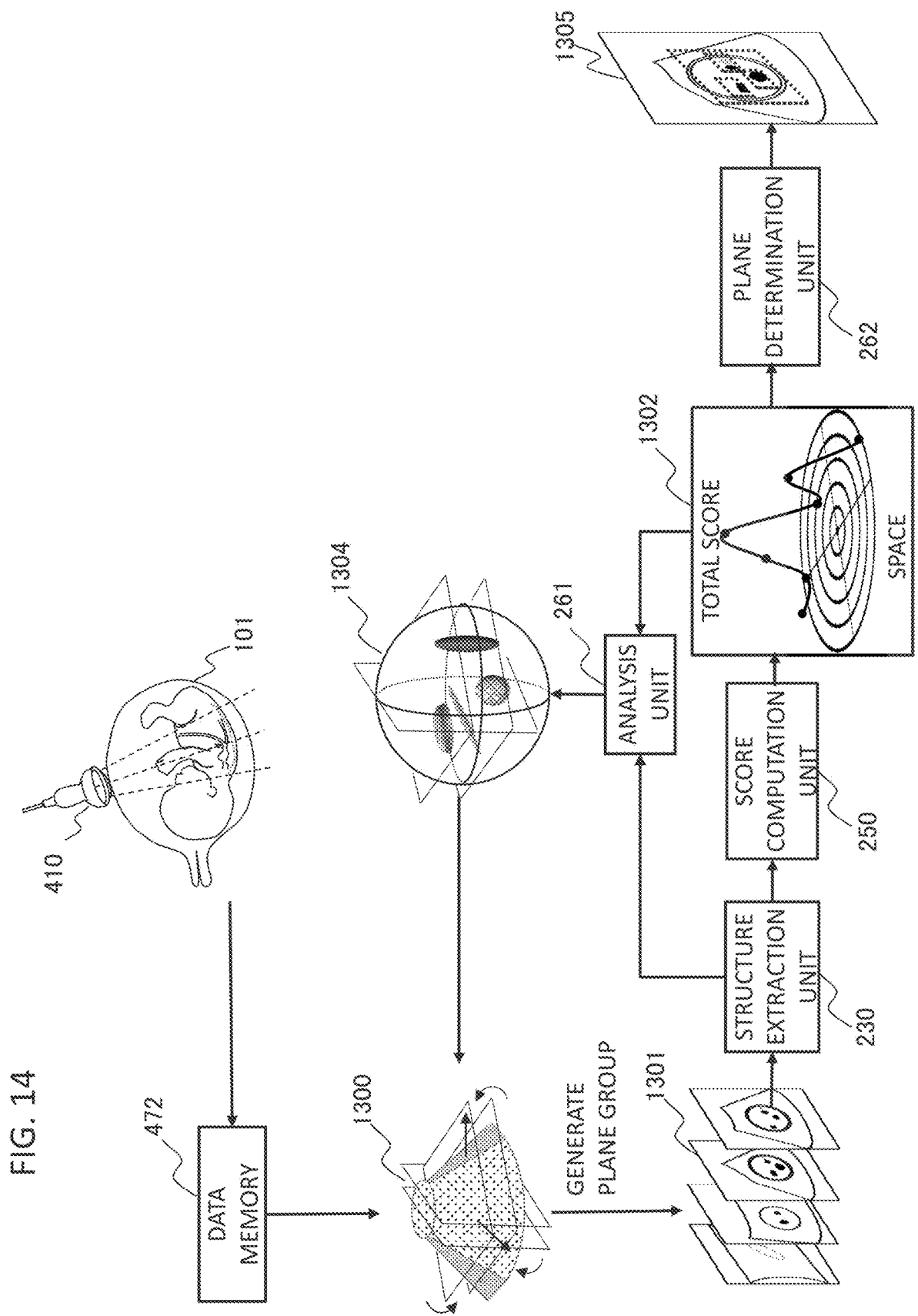
FIG. 14 is a diagram for describing that a plane is extracted by performing structure extraction and score computation from a 3D volume image of the second embodiment.

With reference to FIG. 14, a description will be given of processing of acquiring data, generating a plane group, and selecting a plane of a target plane when an extraction target is 3D volume data. FIG. 15 is referred to as a processing flow.

As illustrated in FIG. 14, the imaging unit 100 uses a mechanical probe or an electronic 2D probe 410 to perform a volume scan on the fetus 101 that is the subject and stores volume data in the data memory 472.

The plane selection unit 231 calls the volume data acquired from the data memory 472, cuts out a plane from a cutting position 1300 in a determined search region, and acquires a target plane group 1302. The cut plane includes a plane perpendicular to an axis of the volume data (Z-axis), a plane parallel to the Z-axis, a plane obtained by rotating these planes in a declination direction or an elevation direction, etc.

The structure extraction unit 230 performs multi-stage extraction of the structure by the same processing as that in steps S1402 to S1405 described above. When the multi-stage extraction is ended, an integration result (image and position information) obtained by integrating the structures detected in multiple stages and the score extraction result is generated, and the score computation unit 250 computes the shape score, the geometric score, and the total score based on the integration result (S1411 to S1413). The structure extraction result and the score computation result are accumulated in a memory (not illustrated) (S1414).

The analysis unit 261 analyzes a temporal change 1302 of the total score on a spatial axis (S1421), further analyzes the spatial distribution of the structure (S1422), and updates the provisional optimal plane (S1423).

The analysis unit 261 generates data 1304 in which an appearance region of the structure is matched with the volume data. The analysis unit 261 determines whether the target plane has been sufficiently narrowed based on the spatial distribution of the structures in the matching data (S1424). When plane acquisition has not ended, a search region for cutting out a subsequent plane group from the volume data 1300 is estimated (S1425) and output to the plane selection unit 231.

When the analysis unit 261 determines that the plane acquisition has ended, the analysis unit 261 determines that the provisional optimal plane is the plane 1205 of the target plane, and outputs the extracted plane 1205, the region extraction result of the structure, and the evaluation score 1204 (S1431 and S1432). The automatic measurement unit 210 performs automatic measurement based on the result of extracting region of the target plane as necessary (S1500).

(Example of Processing Flow of Automatic Measurement Unit 210)

Figure 16:
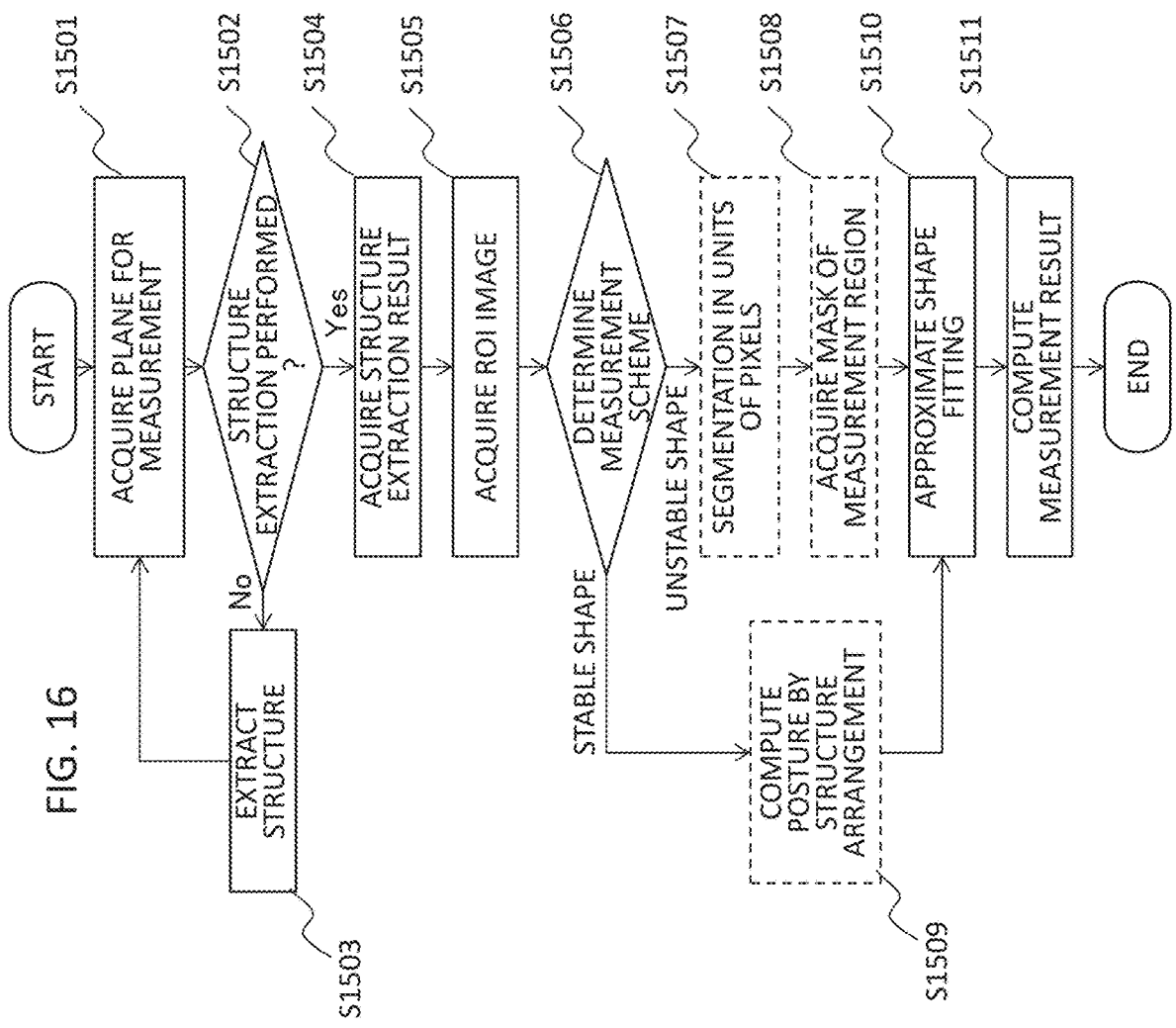
FIG. 16 is a flowchart illustrating a processing process of automatic measurement based on structure extraction according to the second embodiment.

The automatic measurement processing flow of the automatic measurement unit 210 will be described with reference to FIG. 16. This automatic measurement function may be directly connected to a plane extraction function, or may be used as a single automatic measurement function.

First, the automatic measurement unit 210 acquires a plane (S1501), and verifies whether structure extraction has been performed (S1502). When it is determined that structure extraction has not been performed, the automatic measurement unit 210 performs structure extraction again according to the processing flow of FIG. 15 (S1503). As a result, the automatic measurement unit 210 acquires the region extraction result of the structure (S1504).

To narrow down a measurement range in the plane that is the target of automatic measurement, an ROI is set for the target image and an ROI image is generated (S1505). The ROI is set by selecting a region of the structure determined in advance according to the measurement purpose from the region of the structure detected in steps 1402 to 1404. For example, in the case of abdominal AC measurement, the abdomen contour region 910 is cut out from the plane as an ROI.

The automatic measurement unit 210 determines a suitable measurement scheme based on the generated ROI image (image of the measurement part) (S1506), and performs automatic measurement. For example, when a contour of the head, etc. is clear and a shape is relatively stable, a posture in a direction of a head axis (midline), etc. is computed by the structure arrangement (S1509), and an ellipse that is an approximate shape is used to perform contour fitting (S1510), and automatic measurement is performed (S1511).

Further, the automatic measurement unit 210 performs segmentation in units of pixels on a measurement target having a shape instability or shape complexity such as an abdomen or a heart (S1507). A segmentation scheme in units of pixels may correspond to a rule-based scheme such as a template or a decision tree scheme, or may correspond to a scheme of convolution of a feature amount of image and inverse analysis thereof using machine learning. Furthermore, in order to simplify and speed up the processing, a convolution layer inverse analysis using machine learning may be performed. Specifically, the convolution layer of the feature amount obtained in the structure extraction step may be reused without change to relearn only the part of the inverse analysis by transfer learning, etc. The automatic measurement unit 210 acquires a mask of the measurement region based on the segmentation result in units of pixels (S1508), and performs approximate shape fitting (S1510). Based on a fitting result, a measurement result is computed (S1511).

(Description of UI Screen Example)

Figure 17:
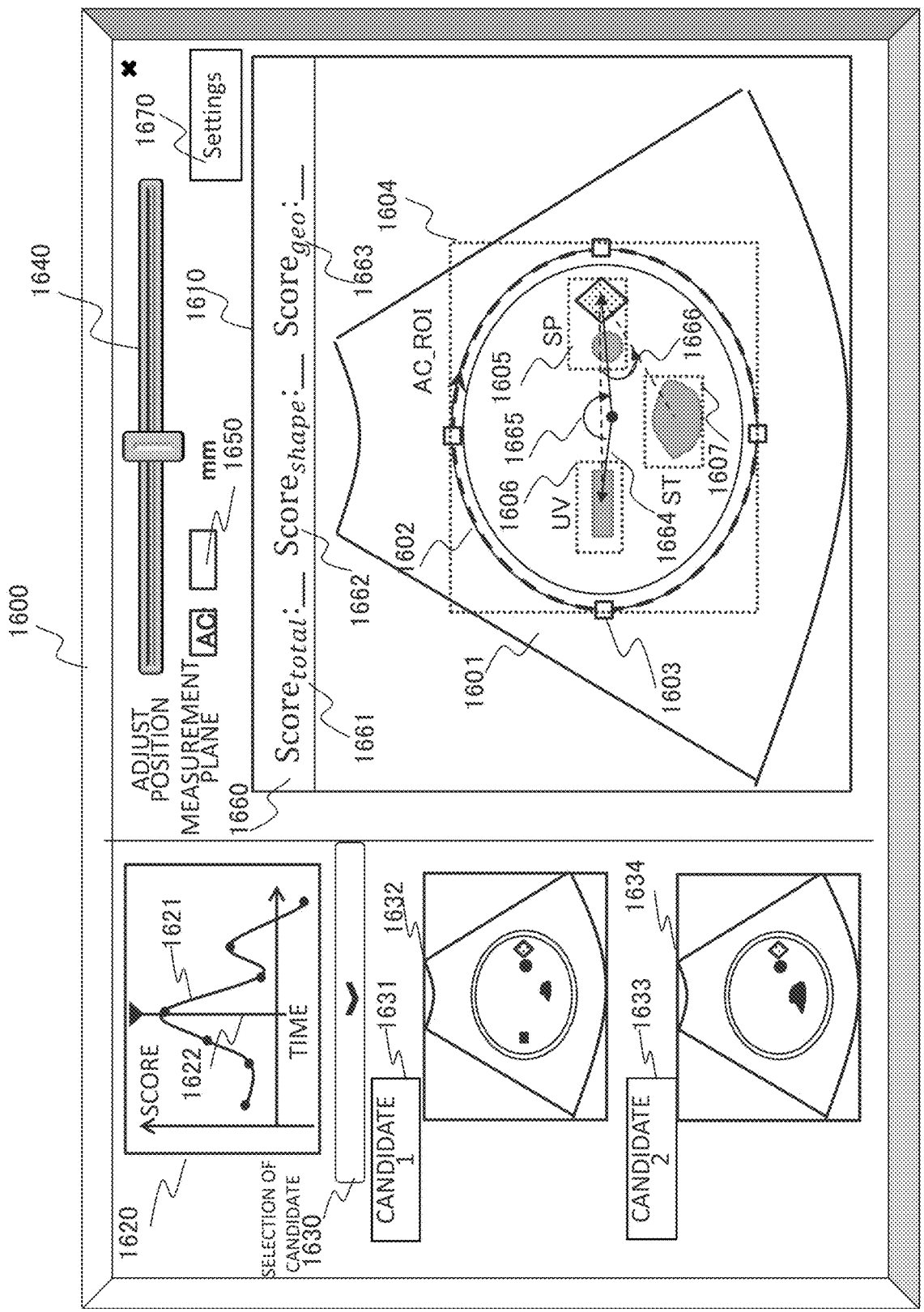
FIG. 17 is a diagram illustrating a graphics user interface (GUI) of a display example of an extracted plane and a structure and plane adjustment in the time-series 2D image of the second embodiment.

An example of a screen (UI) displayed on the display unit 310 is illustrated in FIG. 17. FIG. 17 illustrates an example of a target plane for AC (abdominal circumference) measurement. On a display screen 1600, a target plane display block 1610, an analysis result display 1620, a plane candidate display block 1630, a position adjustment slider 1640, a block 1650 indicating a type or a measurement value of the plane, a block 1660 indicating an appropriate score, a setting block 1670, etc. are displayed. The target plane display block 1610 displays a target plane 1601 extracted by the plane extraction unit 260. In addition, a position 1602 at which measurement is performed on the target plane 1601, and its measurement value 1650 are displayed. A marker 1603 that can be dragged by a user operation is displayed on the measurement position 1602. The measurement position 1602 and the measurement value 1650 are updated by a drag operation of the marker 1603.

A label of the detected structure (a frame indicating a name and a region of the structure) is displayed in a region in which the structure of the target plane 1601 is located. In the case of the abdomen, when an abdomen contour region (AC_ROI) 1604, spine (SP) 1605, an umbilical vein (UV) 1606, and a stomach (ST) 1607 are detected, a label and a reliability score are superimposed and displayed in a predetermined region. A frame indicating a region of each structure superimposed and displayed may correspond to a rectangle indicating a region range or a region mask obtained by inverse analysis of a feature amount of a convolutional layer.

An aptitude score block 1660 of the extracted plane is displayed on the screen. In the aptitude score block, a total score 1661, a shape score 1662, and a geometric score 1663 are displayed. Alternatively, it is possible to display a length of a center of a vein and an abdomen 1664, which is a detailed evaluation standard of the geometric score, an angle 1665 formed by the umbilical vein and the spine around the center of the abdomen, and an angle 1666 formed by the umbilical vein and the abdomen around the spine. As for detailed display setting, by clicking a setting button 1670, a detailed setting screen can be opened and the setting can be changed. The detailed setting screen will be described later with reference to FIG. 20.

In the case of 2D continuous data, a time axis score change 1620 is displayed as auxiliary information display, and an approximate curve 1621 and a display 1622 indicating a time of the selected plane are displayed. The time display 1622 of the selected plane is interlocked with the position adjustment slider 1640. A UI (candidate selection column 1630) for selecting a candidate may be further displayed. When the user desires to change the selected plane, candidate planes 1632 and 1634 that have not been selected are displayed by expanding the candidate selection column 1630. As the candidate planes 1632 and 1634, for example, a plane at a position close to the selected plane of the target plane or a plane having a high total score is displayed. Even though two candidate planes are displayed in FIG. 17, the number of candidate planes may be three or more. Further, buttons 1631 and 16331 may be provided so that any one of the candidate planes can be selected.

For example, the position adjustment slider 1640 is a UI for adjusting the position so that a plane can be extracted from an arbitrary position on the time axis. When the user operates the position adjustment slider 1640, the candidate buttons 1631 and 1633, or the like, the operation input unit 330 transmits a signal to the plane adjustment unit 478 according to the operation. The plane adjustment unit 478 performs a series of processes such as plane update, switching, measurement position update, and measurement value update according to the operation, and displays processing results on the display unit 310.

FIG. 17 illustrates a plane for AC measurement of the abdomen. However, it is desirable that the structure to be displayed is automatically set in accordance with the target plane. Further, it is desirable that details can be changed by setting 1670.

Figure 18:
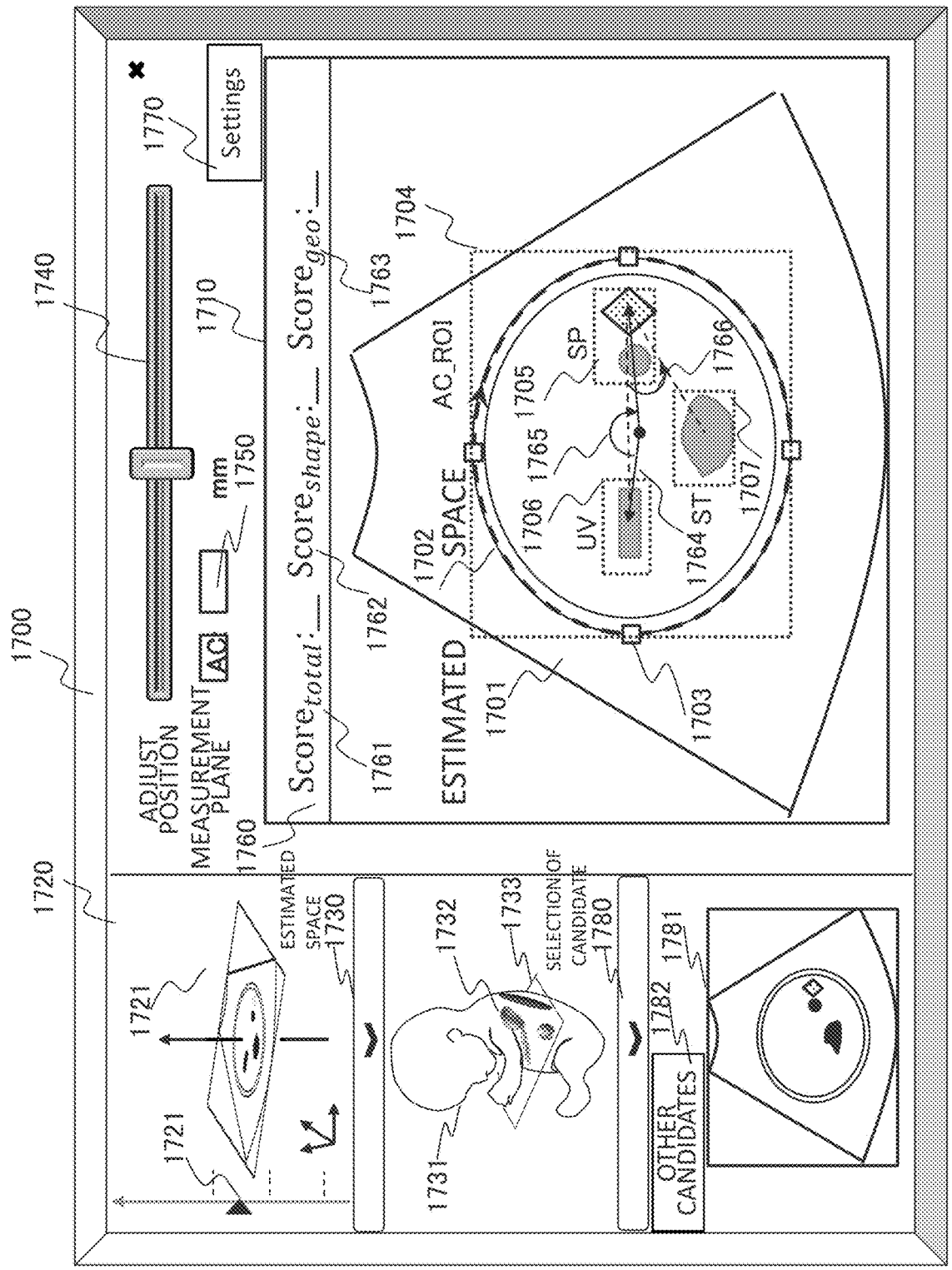
FIG. 18 is a diagram illustrating a GUI of a display example of an extracted plane and a structure and plane adjustment in the 3D volume image of the second embodiment.

FIG. 18 illustrates a screen display example of the plane extracted from the 3D volume. FIG. 18 illustrates an example of a target plane for AC measurement. Similar to FIG. 17, a target plane display block 1710, a spatial plane result display 1720, an estimated space display 170, a candidate display block 1780, a position adjustment slider 1740, a block 1750 indicating a plane type or a measurement value, a block 1760 indicating an appropriate score, a setting block 1770, etc. are displayed on a display screen 1700. The measurement position 1702 and the measurement value 1740 are updated by a drag operation of a marker 1703.

On a target plane 1701, a label of the detected structure (name of the structure and a frame indicating the region) is displayed in a location region. In the case of the abdomen, an abdomen contour region (AC_ROI) 1704, a spine (SP) 1705, an umbilical vein (UV) 1706, and a stomach (ST) 1707 are detected, and labels thereof (frames indicating names and regions) are superimposed and displayed. A reliability score may be superimposed and displayed next to the label of each structure. A frame indicating a region of each structure may correspond to a rectangle indicating a region range or a region mask obtained by inverse analysis of a feature amount of a convolutional layer.

In addition, the aptitude score block 1760 of the extracted plane is displayed. In the aptitude score block, a total score 1761, a shape score 1762, and a geometric score 1763 are displayed. Alternatively, a length of a center of the vein and the abdomen 1764, which is a detailed evaluation standard of the geometric score, an angle 1765 between the umbilical vein and the spine around the abdominal center, and an angle 1766 between the umbilical vein and the stomach around the spine may be displayed. As for the detailed display setting, by clicking a setting button 1770, a detailed setting screen can be opened and the setting can be changed.

As the auxiliary information display, in the case of 3D volume data, a position display bar 1721 indicating a relative position 1721 of the target plane may be displayed in the spatial plane display 1720. Further, a spatial distribution 1732 of the extracted structure and a relative position 1733 of the extracted plane may be displayed in comparison with an approximate model 1731 of the fetus by spatial analysis of the structure. A plurality of arrangements of structures may be simultaneously displayed. In addition, a UI (candidate selection column 1780) for selecting a candidate may be displayed. When the user desires to change the extracted target plane, the candidate selection column 1780 is expanded and a candidate plane 1781 that has not been selected is displayed. Further, a candidate failed to be displayed on the screen may be expanded when the user clicks a candidate button 1782. The candidate plane is, for example, a plane at a position close to the extracted plane or a plane having a high score. Even though one candidate plane is displayed in FIG. 18, the number of candidate planes may be two or more.

Third Embodiment

Figure 19:
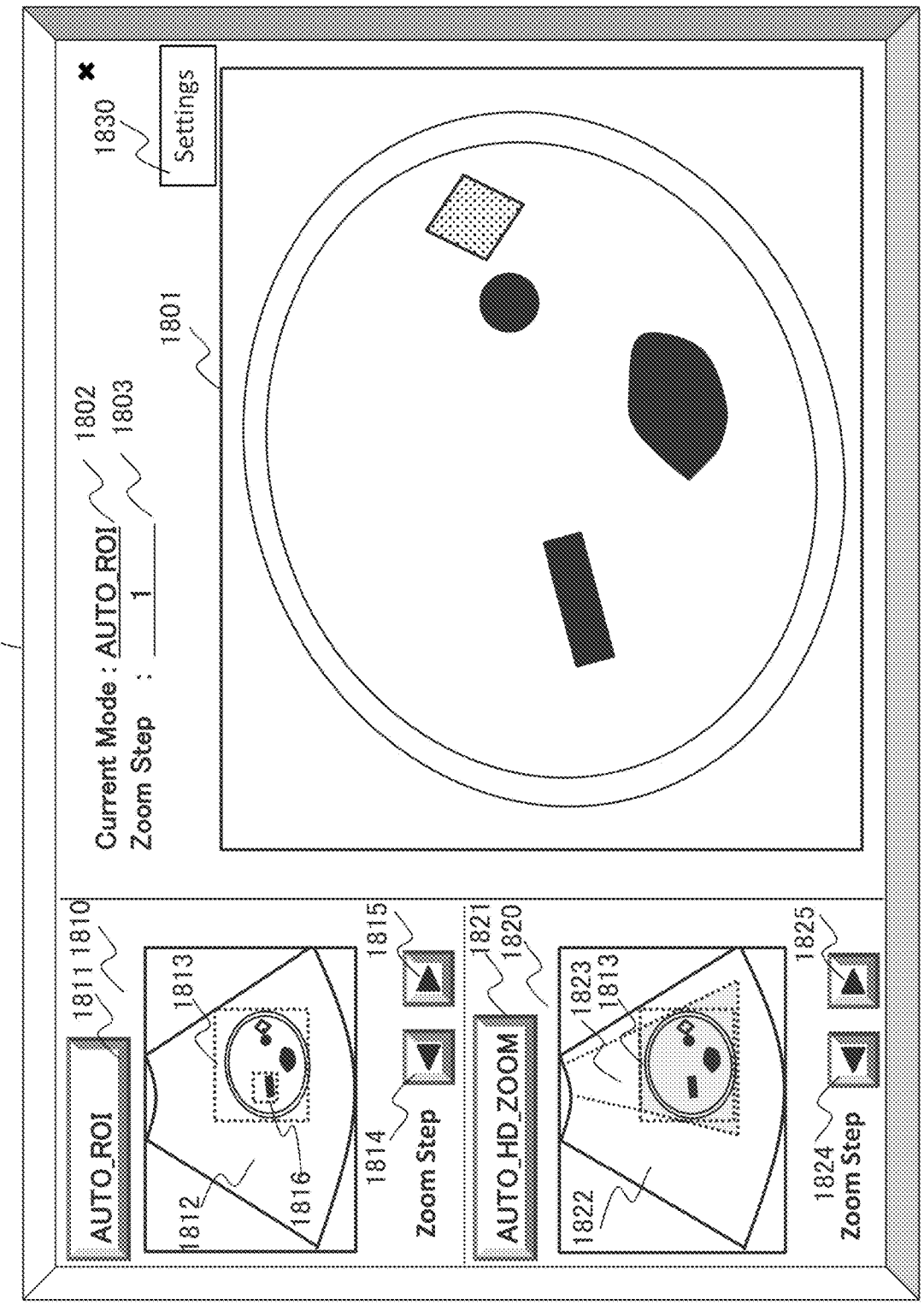
FIG. 19 is a diagram illustrating a GUI of automatic setting of a display region of interest (ROI) and automatic adjustment of an ultrasonic beam scanning range of a captured image of a third embodiment.
Figure 20:
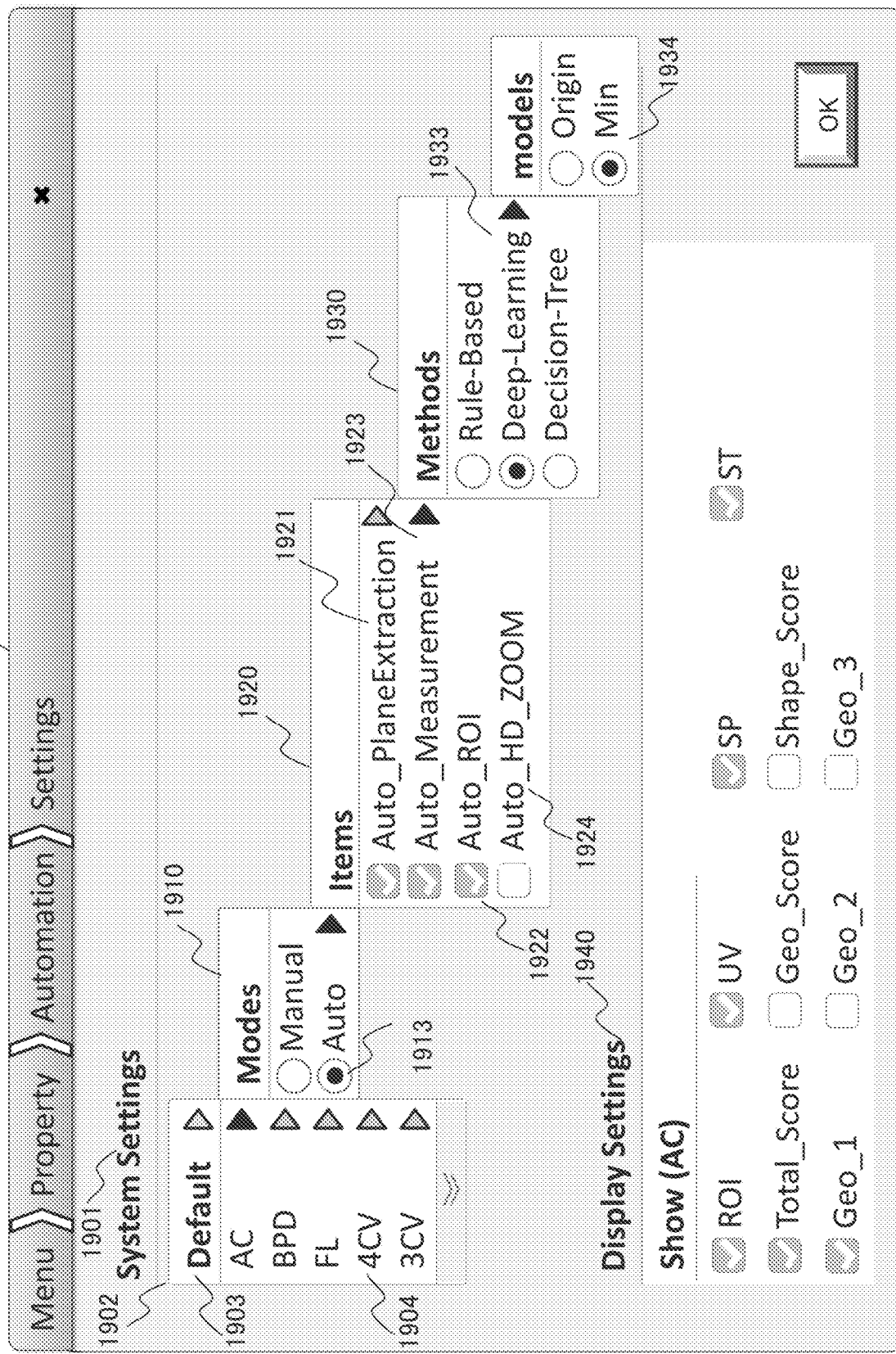
FIG. 20 is a diagram illustrating a detailed setting screen for an automatic function/display function of the third embodiment.
Figure 21:
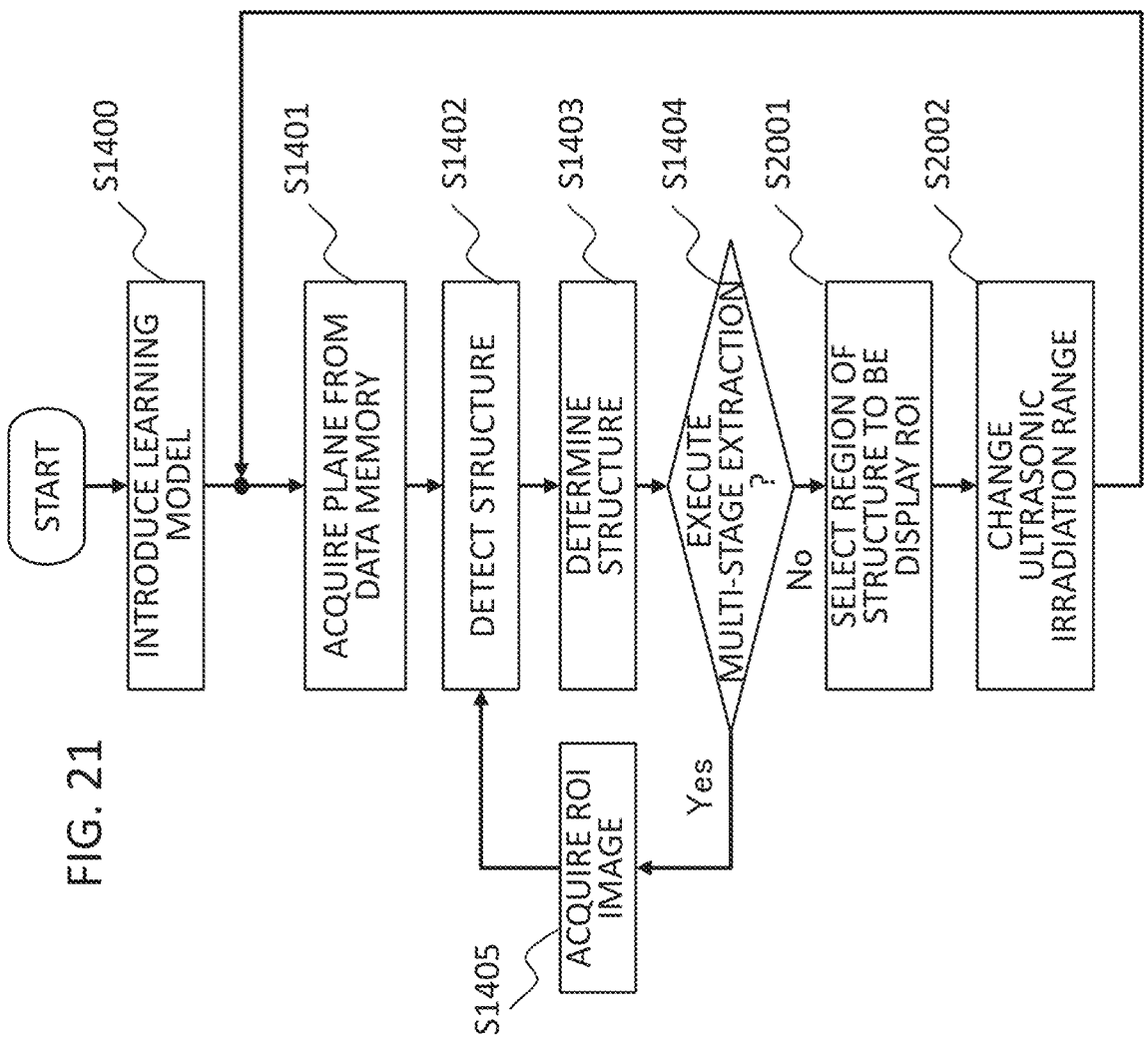
FIG. 21 is a flowchart illustrating a processing process of automatic setting of the display ROI and automatic adjustment of the ultrasonic beam scanning range of the third embodiment.

FIG. 19 to FIG. 21 correspond to a technology for automatic ROI (AUTO_ROI) setting and scanning range automatic adjustment based on structure region detection technologies of the first and second embodiments.

In ultrasonic diagnosis, the size may vary for each subject. In addition, even in the same subject, when a target part is changed during observation, the size may greatly vary. For this reason, an operation of changing a focus position of the probe during observation or manually designating the ROI so as to easily view an observation target on the display screen to perform an enlarged display is frequently performed. Since these operations occur frequently, the convenience of inspection can be improved when automation is achieved.

Therefore, in the third embodiment, since the region of the structure described in the first and second embodiments can be automatically extracted, automatic extraction is used to automatically set the ROI and automatically adjust a scan range of an ultrasonic beam.

Specifically, as in a flow of FIG. 21, steps S1400 to S1404 of FIG. 15 are performed to extract the structure region of the captured plane in multiple stages. Then, the structure extraction unit 230 selects a structure area predetermined according to the target plane or a structure region designated by the user from the extracted structure region and sets the selected region as a display ROI (step S2001). For example, when the target plane is the abdomen, a region 1813 of the abdomen contour is selected as the display ROI as illustrated in FIG. 19. When the user designates a small structure for a region 1816 of the umbilical vein, etc., the designated region is selected as the display ROI. The structure extraction unit 230 outputs the selected display ROI to the display control unit 280. The display control unit 280 enlarges the range of the display ROI in the plane and displays the range on a main display screen 1801 of FIG. 19 of the display unit 310. In this way, the user can observe a screen in which the region of the structure corresponding to the target plane or the region of the structure selected by the user is enlarged as the display ROI.

Meanwhile, the computation unit 210 instructs the imaging unit 100 to narrow a range in which an ultrasonic beam is scanned to a range of the display ROI set by the structure extraction unit 230 in step S2001 (step S2002). Specifically, the computation unit 210 instructs the imaging unit 100 to limit a transmission range of the ultrasonic beam to the range of the display ROI by changing density, range, or focus of a transmission scan line of the ultrasonic transmission beam. In this way, since a scanning range 1823 of the ultrasonic beam is limited to the region of the display ROI range (for example, the region 1813 of the abdomen contour) as illustrated in a screen 1820 of FIG. 19, it is possible to increase an SN ratio of an ultrasonic wave acquired from the region 1813 of the abdomen contour, and it is possible to acquire and display a high-definition image for the region 1813.

FIG. 19 is an example of a screen display for automatic setting of the ROI and automatic adjustment of the scanning range. On the display screen, the main display screen 1801, a display mode setting region 1802 of the main display screen, a display level setting region 1803, an automatic ROI display operation screen 1810, a scanning range automatic adjustment display screen 1820, and a setting button 1830 are displayed.

On the main screen 1801, as described above, the image of the region of the display ROI is enlarged and displayed for easy observation using the region of the structure set in advance or designated by the user as the display ROI.

On the automatic ROI operation screen 1810, a button 1811 for selecting an automatic ROI mode, an original captured image 1812 before setting the automatic ROI, an automatically extracted display ROI (structure region) 1813, and level buttons 1814 and 1815 for an instruction to change the display ROI to a region of a structure of another level undergoing multi-stage extraction are displayed. For example, in the case of observing a fetal heart, after setting a region of a fetal chest contour as the display ROI (AUTO_ROI), an operation of changing the display ROI to the heart region within the fetal chest contour can be performed by operating the button 1815. The region of the image displayed on the main screen 1801 is switched by operating the button 1811 for selecting the automatic ROI mode and the level buttons 1814 and 1815.

Further, a scanning range automatic adjustment mode selection button 1821 (AUTO_HD_ZOOM), an original captured image 1822, an ultrasonic beam scanning range 1823, and buttons 1824 and 1825 for an instruction to change the beam scanning range to a region of a structure of another level undergoing multi-stage extraction are displayed on the scanning range automatic adjustment setting screen 1820. The ultrasonic beam scanning range is switched by an operation of the scanning range automatic adjustment mode selection button 1821 and the level buttons 1824 and 1825.

This screen is set by a button. However, it is possible to adopt a configuration in which automatic setting of the display ROI, automatic adjustment of the ultrasonic beam scanning range, the number of layers to be set, etc. can be set in advance by the user when the user presses the setting button 1830 to open the detailed setting screen. FIG. 20 illustrates an example of the detailed setting screen.

The screen of FIG. 20 includes a screen 1901 for system setting related to processing of the automatic extraction function or automatic measurement function, and a screen 1940 for display setting.

The system setting screen 1901 includes a list 1902 for selecting a measurement target and a list 1910 for selecting a mode as to whether to manually or automatically perform measurement, selection of the target plane, or display setting. For example, the list for selecting the measurement target includes a default 1903 and a list 1904 indicating a plurality of measurement targets. In the example of FIG. 20, the AC is selected as the measurement target. In the mode selection list 1910 of "manual" or "automatic", "automatic" 1913 is selected.

Along with selection of automatic in the mode selection list 1910, a menu 1920 that allows selection of an item to be automatically selected is displayed, and the user selects automatic extraction 1921 of the plane of the target plane, automatic measurement 1923, and automatic setting 1922 of the display ROI. Automatic adjustment 1924 of the scanning range is not selected.

In addition, along with selection of the automatic extraction 1921 of the plane of the target plane, a menu 1930 for selecting an automatic extraction method is displayed, and the user selects deep learning 1933. Along with this selection, a menu 1934 for selecting a size of the learning model for deep learning is further displayed. In the example of FIG. 20, the user selects a reduced model.

In addition, in the display setting screen 1940, along with selection of the AC in the list 1902 for selecting the measurement target, items displayed along with the AC plane are displayed. In the example of FIG. 20, display of the ROI (abdomen contour), the umbilical vein (UV), the spine (SP), the stomach (ST), the total score, and the geometry score of structure 1 has been selected. In addition, the geometric score, the shape score, etc. can be selected.

In FIG. 19, a display ROI automatic setting function and an ultrasonic beam scanning range automatic adjustment function are displayed on the same screen. However, the respective functions may be displayed on separate display screens as independent functions.

According to the present embodiment, a detection model corresponding to a plurality of scales can be generated by learning a reduced model configuration using the multi-scale learning data. In addition, in combination with multi-stage identification, high-speed and high-precision identification is realized using a small learning model. In addition, mounting on the ultrasonic imaging apparatus can be facilitated and the processing speed can be increased.

In addition, by application to the fetal target plane of ultrasound and evaluation of an aptitude degree of a plane by a scoring method using a geometric score that fuses anatomical knowledge of structures focusing on detection of the region of the structure, it is possible to extract a plane close to an image extracted by a doctor as the target plane.

Furthermore, a target measurement value can be automatically measured based on the contour region of the structure.

In addition, analyzing the extracted structure region in time or space allows expansion to navigation that represents a relative position between a probe position and the fetus in time or space, or a relative position between a virtual plane and the fetus.

Furthermore, according to the present embodiment, a plane can be extracted from the 3D volume data, and a location of the detected structure region can be integrated and displayed in the 3D image. As a result, a coarse-fine approach can be adopted with directionality, and a plane search can be performed at high speed and without leakage.

<<Other Modifications>>

The embodiments and modifications thereof are embodiments in which the invention is applied to the ultrasonic diagnostic apparatus. However, the invention can be applied to any medical imaging apparatus capable of acquiring volume data or time-series data. In addition, in the above-described embodiments, a case where the image processing unit 200 is a part of the medical imaging apparatus has been described. However, when imaging and image processing are not performed in parallel, the image processing unit 200 can be used as an image processing apparatus or an image processing unit spatially or temporally arranged apart from the medical imaging apparatus (the imaging unit 100 of FIG. 1). Specifically, the image processing unit 200 can be used as an external device of a medical imaging apparatus such as an existing ultrasonic diagnostic apparatus, and can be used as an apparatus that implements a cloud service such as an application service provider (ASP) or Software as a service (SaaS) connected to an existing medical imaging apparatus via a public line or an Internet line.

Further, the above-described embodiments and modifications have been described in detail for easy understanding of the invention, and are not necessarily limited to the embodiments having all the configurations described.

In addition, a configuration, a function, a processing unit, a processing section, etc. described in an embodiment may be realized by hardware by designing some of all thereof using, for example, an integrated circuit. In addition, each of the above-described configurations, functions, etc. may be realized by software by a processor interpreting and executing a program that realizes each function. Information of a program, a table, a file, etc. for realizing each function can be stored in a recording apparatus such as a memory, a hard disk, or a solid state drive (SSD), or a recording medium such as an IC card, an SD card, or a DVD.

What is claimed is:

1. A medical imaging apparatus comprising:
   an imaging unit that collects image data of a subject; and
   an image processing unit that performs a process of extracting, from the image data collected by the imaging unit, a plane of a target plane that includes a predetermined structure,
   wherein the image processing unit includes a learning model storage unit that stores a learning model learned using learning data, a structure extraction unit that detects a region of the predetermined structure included in the plane by applying the learning model to a plurality of planes obtained from the image data, and a plane extraction unit that extracts the plane of the target plane from the plurality of planes based on the detected region of the predetermined structure,
   wherein the learning data includes a target plane for learning including an image of the structure imaged in advance for the target plane, and a region-of-interest plane for learning obtained by cutting out and enlarging a region of interest including the structure in the target plane for learning,
   wherein the target plane includes, as the predetermined structure, a first structure and a second structure located within the first structure,
   wherein the target plane for learning includes images of the first structure and the second structure,
   wherein the region-of-interest plane for learning is an image obtained by cutting out and enlarging a region of the target plane that includes the first structure of the target plane for learning,
   wherein when a region of the first structure is detected by applying the learning model to the plane obtained from the image data, the structure extraction unit generates an image obtained by cutting out a region including the region of the first structure from the plane, applies the learning model to the cut-out image, and detects a region of the second structure,
   wherein the image processing unit further includes a total score computation unit,
   wherein the structure extraction unit further outputs a first score indicating a reliability of detection for the detected region of the first structure of the plane and a second score indicating a reliability of detection for the detected region of the second structure of the plane,
   wherein the total score computation unit computes:
   a geometric score from a geometric positional relationship between regions of the structures detected by the structure extraction unit, the geometric positional relationship being an angle between two regions of structures, the geometric score being calculated based on the angle and a weight value, and
   a total score which is a summation of the first score indicating the reliability of detection for the detected region of the first structure of the plane, the second score indicating the reliability of detection for the detected region of the second structure of the plane, and the geometric score,
   wherein the plane extraction unit selects the plane, the total score of which is relatively high, as a plane of the target plane,
   wherein the structure extraction unit successively extracts regions of the structure for a plurality of planes obtained from the image data,
   wherein the total score computation unit computes the total score for each of the planes, and
   wherein the plane extraction unit selects a tomographic image of the target plane by analyzing changes in the total score successively computed for the plurality of planes, and causes a display unit to display the selected tomographic image.

2. The medical imaging apparatus according to claim 1, wherein when a region of a structure included in the plane is detected by applying the learning model to the plane obtained from the image data, the structure extraction unit generates an image obtained by cutting out a region including the region of the structure from the plane and further detects a structure included in the cut-out image by applying the learning model again.

3. The medical imaging apparatus according to claim 1, wherein the learning data further includes information specifying a type of the structure and position information of a region in which the structure is located on an image, each of which is associated with the target plane for learning or the region-of-interest plane for learning including the structure.

4. The medical imaging apparatus according to claim 1, wherein the learning model is a reduced model, in which at least one of an input image size and the number of levels of a high-accuracy model learned using the target plane as learning data is reduced based on analysis of a relative size of a detection target region, relearned using the learning data including the target plane for learning and the region-of-interest plane for learning.

5. The medical imaging apparatus according to claim 4, wherein when the learning model is the reduced model in which the input image size is reduced, the structure extraction unit reduces the plane obtained from the image data to the input image size and inputs the plane to the learning model as an input image.

6. The medical imaging apparatus according to claim 1, wherein the image processing unit further includes an automatic measurement unit that computes a measurement value determined in advance using a region of the structure of the plane selected as a plane of the target plane.

7. The medical imaging apparatus according to claim 1, wherein the image processing unit further includes a display control unit that causes a display unit to display a plane of the target plane selected by the plane extraction unit, a region of the structure, and the total score.

8. The medical imaging apparatus according to claim 1, wherein the structure extraction unit selects one of a plurality of detected regions of the structure as a region of interest.

9. The medical imaging apparatus according to claim 8, further comprising
a display control unit that causes a display unit to enlarge and display a region of the plane corresponding to the region of interest selected by the structure extraction unit.

10. The medical imaging apparatus according to claim 8, wherein the imaging unit collects the image data by transmitting an ultrasonic beam while scanning a subject, and
the imaging unit limits a scanning range of the ultrasonic beam to a range of the region of interest selected by the structure extraction unit.

11. An image processing apparatus for performing a process of receiving image data from a subject and extracting, from the image data, a plane of a target plane that includes a predetermined structure, the image processing apparatus comprising:
a learning model storage unit that stores a learning model learned using learning data;
a structure extraction unit that detects a region of the predetermined structure included in the plane by applying the learning model to a plurality of planes obtained from the image data; and
a plane extraction unit that extracts the plane of the target plane based on the detected region of the predetermined structure,
wherein the learning data includes a target plane for learning including an image of the structure captured in advance for the target plane, and a region-of-interest plane for learning obtained by cutting out and enlarging a partial region including the structure in the target plane for learning,
wherein the target plane includes, as the predetermined structure, a first structure and a second structure located within the first structure,
wherein the target plane for learning includes images of the first structure and the second structure,
wherein the region-of-interest plane for learning is an image obtained by cutting out and enlarging a region of the target plane that includes the first structure of the target plane for learning,
wherein when a region of the first structure is detected by applying the learning model to the plane obtained from the image data, the structure extraction unit generates an image obtained by cutting out a region including the region of the first structure from the plane, applies the learning model to the cut-out image, and detects a region of the second structure,
wherein the image processing unit further includes a total score computation unit,
wherein the structure extraction unit further outputs a first score indicating a reliability of detection for the detected region of the first structure of the plane and a second score indicating a reliability of detection for the detected region of the second structure of the plane,
wherein the total score computation unit computes:
a geometric score from a geometric positional relationship between regions of the structures detected by the structure extraction unit, the geometric positional relationship being an angle between two regions of structures, the geometric score being calculated based on the angle and a weight value, and
a total score which is a summation of based on the first score indicating the reliability of detection for the detected region of the first structure of the plane, the second score indicating the reliability of detection for the detected region of the second structure of the plane, and the geometric score,
wherein the plane extraction unit selects the plane, the total score of which is relatively high, as a plane of the target plane,
wherein the structure extraction unit successively extracts regions of the structure for a plurality of planes obtained from the image data,
wherein the total score computation unit computes the total score for each of the planes, and
wherein the plane extraction unit selects a tomographic image of the target plane by analyzing changes in the total score successively computed for the plurality of planes, and causes a display unit to display the selected tomographic image.

\* \* \* \* \*